(12) United States Patent
Vago et al.

(10) Patent No.: US 7,258,747 B2
(45) Date of Patent: Aug. 21, 2007

(54) MULTI-MOTION STAINBRUSH

(75) Inventors: James Charles Vago, Newport, KY (US); Stephen Allen Jacobs, Fairfield, OH (US); Paul Amaat Raymond Gerard France, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 665 days.

(21) Appl. No.: 10/659,868

(22) Filed: Sep. 11, 2003

(65) Prior Publication Data

US 2004/0084063 A1    May 6, 2004

Related U.S. Application Data

(60) Provisional application No. 60/409,861, filed on Sep. 11, 2002.

(51) Int. Cl.
*B08B 7/04*    (2006.01)

(52) U.S. Cl. .......... 134/6; 134/25.2; 134/25.4; 134/40; 134/42; 15/22.1; 15/22.2; 15/22.4; 15/28

(58) Field of Classification Search .......... 15/22.1, 15/22.2, 28, 22.4; 134/6, 25.2, 25.4, 40, 134/42
See application file for complete search history.

(56) References Cited

U.S. PATENT DOCUMENTS

| | | | | |
|---|---|---|---|---|
| 2,740,977 | A | * | 4/1956 | Allen .......... 15/24 |
| 3,055,031 | A | | 9/1962 | Raclin |
| 4,177,532 | A | | 12/1979 | Azuma |
| 4,223,418 | A | | 9/1980 | Pedrini |
| 4,574,414 | A | | 3/1986 | Zhadanov |
| 4,724,564 | A | * | 2/1988 | Fresh .......... 15/36 |
| 4,841,590 | A | | 6/1989 | Terry et al. |
| 5,153,962 | A | | 10/1992 | Ritter |
| 5,156,634 | A | | 10/1992 | Yang |
| 5,186,627 | A | * | 2/1993 | Amit et al. .......... 433/216 |
| 5,333,337 | A | | 8/1994 | Markley |

(Continued)

FOREIGN PATENT DOCUMENTS

DE    3 615 918 A1    11/1987

(Continued)

OTHER PUBLICATIONS

Patent Abstracts of Japan, Vo. 017, No. 523 (C-1113), Sep. 21, 1993.

(Continued)

*Primary Examiner*—Sharidan Carrillo
(74) *Attorney, Agent, or Firm*—Julia A. Glazer; Brahm J. Corstanje; Kim William Zerby

(57) ABSTRACT

A method of using an electric stainbrush for cleaning inanimate surfaces is provided. The electric stainbrush includes a handle having a motor disposed therein, a head having a longitudinal axis, and a neck disposed between the handle and the head. First and second bristle holders are associated with the head. The first bristle holder oscillates or rotates. The second bristle holder reciprocates in generally the same direction as the longitudinal axis of the head but does not rotate or oscillate. The motor is operatively connected to the first and second bristle holders.

14 Claims, 17 Drawing Sheets

U.S. PATENT DOCUMENTS

| | | | |
|---|---|---|---|
| 5,345,640 A | 9/1994 | Goss | |
| 5,353,461 A | 10/1994 | Enriquez | |
| 5,418,996 A | 5/1995 | Chen | |
| 5,423,102 A | 6/1995 | Madison | |
| 5,504,959 A * | 4/1996 | Yukawa et al. | 15/22.1 |
| 5,524,312 A * | 6/1996 | Tan et al. | 15/22.1 |
| 5,701,625 A | 12/1997 | Siman | |
| 5,707,163 A | 1/1998 | Gregory | |
| 5,718,014 A | 2/1998 | DeBlois et al. | |
| 5,850,655 A * | 12/1998 | Gocking et al. | 15/28 |
| 5,864,911 A | 2/1999 | Arnoux et al. | |
| 5,870,790 A | 2/1999 | Root et al. | |
| 5,950,268 A | 9/1999 | Murphy et al. | |
| 5,956,792 A | 9/1999 | Gutelius et al. | |
| 6,000,083 A | 12/1999 | Blaustein et al. | |
| 6,000,626 A | 12/1999 | Futo et al. | |
| 6,020,300 A | 2/2000 | Tcheou et al. | |
| 6,032,313 A | 3/2000 | Tsang | |
| 6,059,475 A | 5/2000 | Jafarmadar | |
| 6,170,107 B1 | 1/2001 | George et al. | |
| 6,170,108 B1 | 1/2001 | Knight | |
| 6,178,579 B1 | 1/2001 | Blaustein et al. | |
| 6,189,693 B1 | 2/2001 | Blaustein et al. | |
| 6,210,064 B1 | 4/2001 | White et al. | |
| 6,253,405 B1 | 7/2001 | Gutelius et al. | |
| 6,295,681 B1 | 10/2001 | Dolah | |
| 6,311,837 B1 | 11/2001 | Blaustein et al. | |
| 6,376,444 B1 * | 4/2002 | Hortel et al. | 510/277 |
| 6,499,174 B2 | 12/2002 | Henrie | |
| 6,648,641 B1 * | 11/2003 | Viltro et al. | 433/80 |
| 6,725,490 B2 * | 4/2004 | Blaustein et al. | 15/22.2 |
| 6,928,685 B1 * | 8/2005 | Blaustein et al. | 12/22.1 |
| 2002/0112741 A1 | 8/2002 | Pieroni et al. | |
| 2002/0129835 A1 | 9/2002 | Pieroni et al. | |
| 2003/0066145 A1 * | 4/2003 | Prineppi | 15/22.1 |
| 2003/0084524 A1 | 5/2003 | Blaustein et al. | |
| 2003/0084525 A1 | 5/2003 | Blaustein et al. | |
| 2003/0084526 A1 | 5/2003 | Brown | |
| 2003/0084527 A1 * | 5/2003 | Brown et al. | 15/22.1 |
| 2003/0084528 A1 | 5/2003 | Chan et al. | |
| 2003/0126699 A1 | 7/2003 | Blaustein et al. | |
| 2003/0140437 A1 * | 7/2003 | Eliav et al. | 15/22.2 |
| 2003/0163882 A1 * | 9/2003 | Blaustein et al. | 15/22.2 |
| 2003/0182744 A1 * | 10/2003 | Fattori et al. | 15/22.1 |
| 2004/0083566 A1 * | 5/2004 | Blaustein et al. | 15/22.1 |
| 2005/0000045 A1 * | 1/2005 | Blaustein et al. | 15/22.1 |
| 2005/0005375 A1 * | 1/2005 | Blaustein et al. | 15/22.2 |
| 2005/0005376 A1 * | 1/2005 | Blaustein et al. | 15/22.2 |
| 2005/0066996 A1 * | 3/2005 | France et al. | 134/6 |
| 2005/0091771 A1 * | 5/2005 | Blaustein et al. | 15/22.1 |
| 2005/0199265 A1 * | 9/2005 | France et al. | 134/6 |
| 2006/0032006 A1 * | 2/2006 | Brown et al. | 15/22.1 |
| 2006/0191085 A1 * | 8/2006 | Brown et al. | 15/22.1 |
| 2006/0254006 A1 * | 11/2006 | Blaustein et al. | 15/22.2 |
| 2006/0288505 A1 * | 12/2006 | Blaustein et al. | 15/22.1 |

FOREIGN PATENT DOCUMENTS

| | | |
|---|---|---|
| JP | 05146313 | 6/1993 |
| JP | 11-032971 | 2/1999 |
| WO | WO 02/49497 A2 | 6/2002 |

OTHER PUBLICATIONS

Whitey Pika UW-8000 Handy Type Ultrasonic Wave Point Stain Remover from Kumazaki-Aim Company—Dec. 2003.

Bissell-to-Go Spot Scrubber from www.greenfieldonline.com- on or about Nov. 12, 2003.

* cited by examiner

MULTI-MOTION STAINBRUSH

CROSS REFERENCE TO RELATED APPLICATIONS

This application claims the benefit of U.S. Provisional Application Ser. No. 60/409,861, filed Sep. 11, 2002.

FIELD

The present invention relates to stain-removal brushes for fabrics or inanimate hard surfaces. More specifically, the invention relates to electrically powered stain-removal brushes for fabrics or inanimate hard surfaces.

BACKGROUND

The art is replete with techniques for transforming the rotational output of a motor or other electromotive power source into desired brushing motions. Many techniques include a shaft as a component of the drive train. The shaft may rotate, oscillate, or reciprocate. The shaft is coupled to a bristle holder. Most often, the bristle holder is driven by the shaft in a rotating or oscillating manner about an axis which is normal to the longitudinal axis of the shaft.

Such electric brushes typically provide only a single brushing motion. While single brushing motions are beneficial, it believed that multi-motion electric brushes can provide superior cleaning action. Further, there is a desire to combine the cleaning action provided by the bristles of a rotating or oscillating bristle holder with the cleaning action of bristles that only reciprocate along a longitudinal axis of the electric stainbrush so as to more closely replicate a manual brushing motion.

SUMMARY

The present invention is directed to a method of cleaning an inanimate surface comprising a) having an electric stainbrush, wherein the electric stainbrush comprises i) a handle having a motor disposed therein; ii) a head having a longitudinal axis; iii) a neck disposed between the handle and the head; iv) a first bristle holder associated with the head which oscillates or rotates; v) a second bristle holder associated with the head which reciprocates in generally the same direction as the longitudinal axis of the head but does not rotate or oscillate; vii) a first set of bristles associated with the first bristle holder; and viii) a second set of bristles associated with the second bristle holder; wherein the motor is operatively connected to the first and second bristle holders; b) putting an aqueous solution in contact with the inanimate surface; and c) employing the electric stainbrush to brush the aqueous solution on the inanimate surface.

The present invention is further directed to an article of commerce comprising the electric stainbrush in association with a set of instructions, wherein the instructions direct a user of the electric stainbrush to i) put an aqueous solution in contact with the inanimate surface, and ii) employ the electric stainbrush to brush the aqueous solution on the inanimate surface. The present invention may also include an absorbent stain receiver article.

The present invention is yet further directed to a kit. The kit contains the necessary materials to enable a consumer to clean an inanimate surface such as the electric stainbrush of the present invention and a cleaning solution. The kit may also include one or more absorbent stain receiver article(s). Instructions that instruct a consumer how to use the kit may also be included.

These and other features, aspects, and advantages of the present invention will become evident to those skilled in the art from a reading of the present disclosure.

BRIEF DESCRIPTION OF THE DRAWINGS

It is believed that the present invention will be better understood from the following description taken in conjunction with the accompanying drawings in which:

FIG. 19 is a photographic side elevational view of the stainbrush head of FIG. 18;

DETAILED DESCRIPTION OF THE INVENTION

Figure 1:
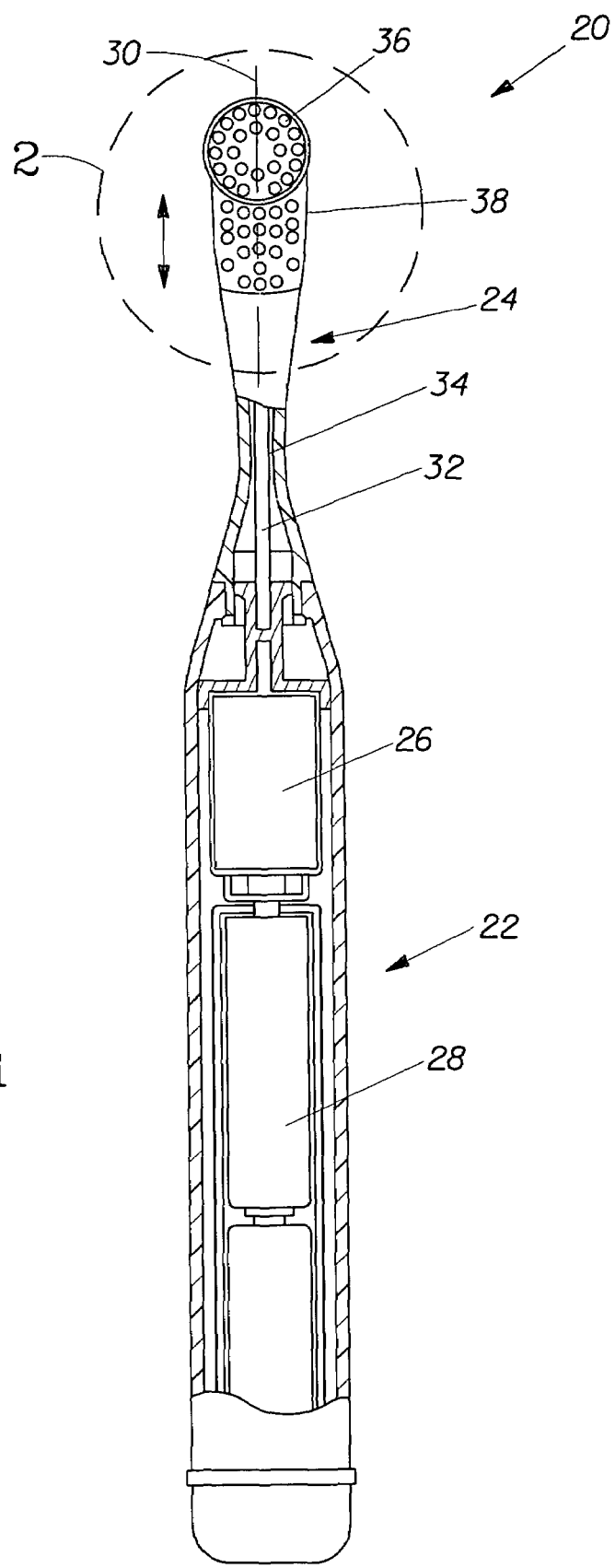
FIG. 1 is a planar, partial sectional, top view of an electric stainbrush made in accordance with the present invention, wherein the electric stainbrush incorporates a rotating or oscillating shaft.

Reference will now be made in detail to various embodiments of the present invention, examples of which are illustrated in the accompanying drawings wherein like numerals indicate the same elements throughout the views and wherein numerals having the same last two digits (e.g., 20 and 120) connote similar or corresponding elements.

All documents cited are, in relevant part, incorporated herein by reference; the citation of any document is not to be construed as an admission that it is prior art with respect to the present invention.

Except as otherwise noted, all amounts including quantities, percentages, portions, and proportions, are understood to be modified by the word "about", and amounts are not intended to indicate significant digits.

Except as otherwise noted, the articles "a", "an", and "the" mean "one or more".

Herein, "comprising" means that other steps and other ingredients which do not affect the end result can be added. This term encompasses the terms "consisting of" and "consisting essentially of". The compositions and methods/processes of the present invention can comprise, consist of, and consist essentially of the essential elements and limitations of the invention described herein, as well as any of the additional or optional ingredients, components, steps, or limitations described herein.

Herein, "inanimate surface" means a surface that does not make up a part of a living organism (e.g., does not include teeth). Examples of inanimate surfaces include, but are not limited to, fabrics and hard surfaces.

Herein, "stainbrush" means a brush for cleaning an inanimate surface.

A. Stainbrush

As will be appreciated, the present invention is directed to electric stainbrushes (including electric stainbrushes having replaceable heads) and electric stainbrush heads having first and second moving bristle holders. The first bristle holder rotates or oscillates while the second bristle holder reciprocates in the longitudinal direction of the head. In a more preferred form, the first bristle holder rotates or oscillates but does not reciprocate, translate, or perform any other non-rotational or oscillatory motion, and the second bristle holder reciprocates but does not rotate or oscillate. Herein, the term "rotate" is intended to refer to a unidirectional angular motion (e.g., a constant clockwise motion) while the term "oscillate" is intended to refer to vibratory angular motion (e.g., repeated cycles of clockwise rotation and counter clockwise rotation). Vibration is any periodic movement having repeated cycles. Vibratory motion can have one or more frequencies and amplitudes. Vibratory motion that is substantially linear is referred to herein as a reciprocating motion.

The present invention can be used in combination with electric stainbrushes and electric stainbrush heads that include shafts that rotate, oscillate, or reciprocate (as well as combinations thereof) to impart motion to the first and second bristle holders. In addition, the present invention can be used in combination with electric stainbrushes and electric stainbrush heads where the shaft is operatively connected to both the first and second bristle holders or only one of the bristle holders. In the latter instance, the bristle holders are themselves interconnected so that a motion is imparted to the bristle holder that is not directly coupled to the shaft.

Referring to FIGS. 1 to 9, some exemplary electric stainbrushes made in accordance with the present invention will now be described. These electric stainbrushes utilize a shaft that rotates. While these embodiments will be described with respect to the particular motor and shaft arrangement illustrated in FIG. 1 for purposes of simplicity and clarity, it will be appreciated that other motor and rotating (or oscillating) shaft arrangements can be substituted. For example, U.S. Pat. Nos. 5,617,603; 5,850,603; 5,974,615; 6,032,313; 5,732,432; 5,070,567; 5,170,525; 5,416,942; 3,588,936; 5,867,856; and 4,397,055, disclose other motor and rotating or oscillating shaft arrangements that might be suitable.

Turning to FIG. 1, the electric stainbrush comprises a stainbrush head 20, a body or handle 22, and an elongated neck 24 there between. Herein, the term "forward" is intended to refer to the direction from the handle to the head while the term "rearward" is intended to refer to the direction from the head to the handle. In addition, the term "longitudinal" is intended to refer to a lengthwise feature of an element as seen from a top planar view thereof. For example, a longitudinal axis is an axis passing through the longest dimension of an element, such as the head or a shaft. A longitudinal direction is a direction that generally corresponds to a longitudinal axis but which may not lie in the same plane as the longitudinal axis. For example, the longitudinal axes of a shaft and a stainbrush head may not lie in the same plane but generally extend in the same direction from a top planar view. Similarly, a neck and head that are angled with respect to each other may not have longitudinal axes which lie in the same plane, but do have axes which extend in the same general longitudinal direction from a top planar view. The electric stainbrushes of the present invention typically have an elongate head with a longitudinal axis passing through the longest dimension thereof. This axis typically extends in the same general direction as the longitudinal axes of the stainbrush neck and/or shaft. By the phrase "same general direction", some angular deviation is contemplated between the axes. The second bristle holder of these stainbrushes reciprocates in the same general direction as one or more of these axes. More preferably, the second bristle holder of these stainbrushes reciprocates in substantially the same or the same direction as one or more of these axes, although hereafter for simplicity only reciprocation in the same general direction is discussed.

The handle is hollow and includes a motor 26 and batteries 28 for powering the motor. A rechargeable power source can be substituted for the batteries. The head 20 has a longitudinal axis 30 passing there through. The longitudinal axis 30 extends in the same general longitudinal direction as a longitudinal axis 32 of a shaft 34. The shaft 34 is housed at least partially within neck 24. A first bristle holder 36 is disposed at a first end of the head 20, wherein the first end is at the forward most point of the head 20. While the first bristle holder 36 is illustrated as circular in shape, other shapes can be utilized. Further, while the first bristle holder 36 is disposed at the first end of the head 20, it will be appreciated that it can be disposed away from the first end and other features, such as stationary bristles, might be disposed between the first bristle holder 36 and the first end of the head 20. The first bristle holder 36 includes at least one slot for receiving a remote most end of the rotating shaft 34, as described in U.S. Pat. No. 5,625,916. The remote-most end of the shaft 34 is bent or offset from the longitudinal axis 32 of the shaft 34 and engages the slot to oscillate the first bristle holder 36 about a pin (not shown). In other words, the first bristle holder 36 oscillates about an axis approximately normal to the longitudinal axis 30, 32 of the head 20 and/or the shaft 34. In this embodiment, the first bristle holder only oscillates and does not reciprocate, translate, or perform any other non-rotational motion.

A second bristle holder 38 is disposed adjacent the first bristle holder 36. The second bristle holder 38 reciprocates in the same general longitudinal direction as longitudinal axis 30 of the head 20. In this embodiment, the longitudinal direction of reciprocation is also the same as the longitudinal direction of the longitudinal axis 32 of the shaft 34. While it is desirable to locate the second bristle holder 38 directly adjacent the first bristle holder 36, it is contemplated that a gap may be provided between the first and second bristle holders. In addition, the gap between the first and second bristle holders might be filled with stationary bristles which are embedded in fixed or stationary third bristle holder (not shown) which forms part of the stainbrush head. Further, while the first bristle holder 36 has been described as adjacent the first end of the head 20, it is contemplated that the second bristle holder 38 might be disposed adjacent the first end of the head 20 and driven in the same manner as described below with respect to FIG. 2.

In addition, the electric stainbrush of FIG. 1 might be provided with a replaceable head. A suitable arrangement that can be adapted to the present invention is disclosed in U.S. Pat. No. 5,617,601.

Figure 2:
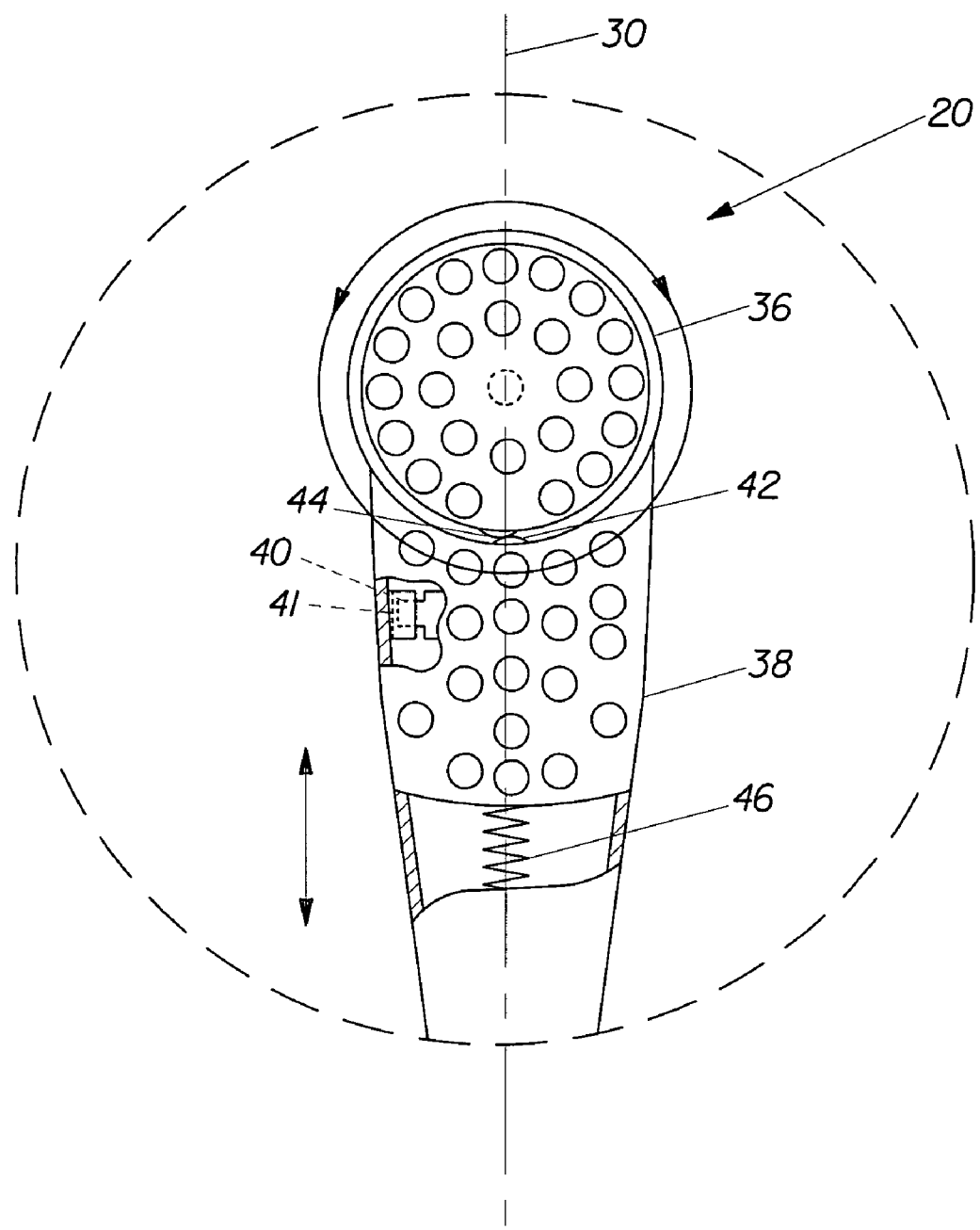
FIG. 2 is a planar, partial section top view of a first embodiment of a stainbrush head suitable for use with the electric stainbrush of FIG. 1.

Referring to FIG. 2, a first embodiment of a stainbrush head suitable for use with the electric stainbrush of FIG. 1 will now be described in more detail. The second bristle holder 38 has a pair of opposed projections 40, one of which is illustrated, which are slideably received by slots 41, one of which is illustrated, of the head 20 to guide the second bristle holder 38 in its longitudinal motion. The slots are aligned in generally the same longitudinal direction as the longitudinal axis of the head 20. The second bristle holder 38 is driven in a reciprocating longitudinal motion by the movement of the first bristle holder 36 through a pair of opposed hemispherical protrusions 42, 44 that engage one another to displace the second bristle holder 38 against a biasing element, such as spring 46. As the protrusions cyclically engage and disengage each other as the first bristle holder 36 oscillates, the second bristle holder 38 is moved away from and then back toward the first bristle holder 36 with the cooperation of the spring 46. The protrusions are rigidly mounted to or integrally formed with the first and second bristle holders. As the motor 26 of the electric stainbrush rotates the shaft 34, the remote end of the shaft engages the slot of the first bristle holder 36 to oscillate the first bristle holder. As the first bristle holder 36 oscillates, the protrusion 44 disposed on the first bristle holder 36 comes into contact with the surface of the protrusion 42 on the second bristle holder 38, thereby displacing the second bristle holder 38 away from the first bristle holder in the same longitudinal direction as the longitudinal axis of the head 20. As the shaft 34 continues to rotate, the protrusion 44 of the first bristle holder 36 disengages from the other protrusion 42 so that the spring 46 can urge the second bristle holder 38 back toward the first bristle holder 36, thus completing one cycle. As the first bristle holder 36 reverses its direction of rotation, this cycle is repeated.

Figure 3:
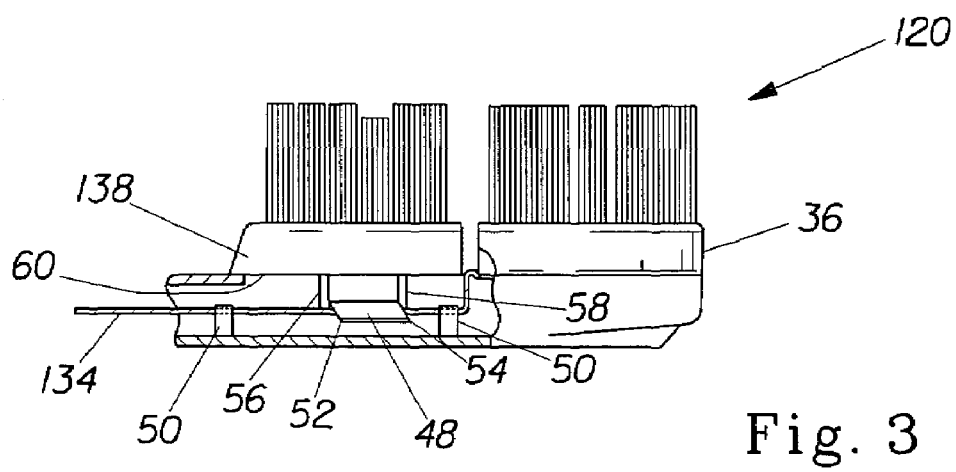
FIG. 3 is an elevational, partial sectional side view of a second embodiment of a stainbrush head suitable for use with the electric stainbrush of FIG. 1.

Referring to FIG. 3, a second embodiment of a stainbrush head suitable for use with the electric stainbrush of FIG. 1 will now be described. The head 120 also includes a second bristle holder 138 that is slideably mounted in slots (not shown, but which can be the same arrangement as the projection 40 and slot 42 arrangement illustrated in FIG. 2). The second bristle holder 138 is reciprocatingly driven in the same general longitudinal direction as the longitudinal axis of the head 20 and/or shaft 134. A cam 48 included on the shaft 134 operatively interconnects the shaft 134 with second bristle holder 138. Optionally, the shaft 134 can be supported by shaft supports 50. The shaft supports 50 may include C or U shaped portions (not shown) that receive the shaft 134. Other means for retaining the shaft 134 in a support are known in the art. The cam 48 can comprise a shaped element or bead, with an appropriate eccentric configuration, placed or molded over and firmly secured to the shaft 134. In one arrangement, the cam 48 is cylindrically shaped with a pair of acutely angled surfaces 52, 54 which are inclined in the same direction and at the same angle of inclination, but which are disposed at opposite ends of the cam 48. In other words, the angled surfaces 52, 54 are merely the surface resulting from a diagonal slice through the cylinder of the cam 48. The direction of inclination and angle of inclination can be varied as desired to change the frequency and stroke of the second bristle holder 138. First and second cam followers 56, 58 depend from a bottom surface 60 of the second bristle holder 138. The cam followers 56, 58 are offset or spaced from each other so that cam 48 is disposed between the cam followers 56, 58 which straddle and/or capture the cam 48. The angled surfaces 52, 54 of the cam 48 slidingly engage the free ends of the cam followers 56, 58. As the shaft 134 rotates, the first acutely angled surface 52 of the cam 48 comes into contact with a surface of the first cam follower 56 and drives the cam follower, and therefore, the second bristle holder 138, away from the first bristle holder 36 in a direction generally the same as the direction of the longitudinal axis of the head 120. The second bristle holder 138 is guided by the longitudinally extending slots. As the shaft 134 continues to rotate, the cam 48 disengages from the first cam follower 56. The second acutely angled second surface 54 of the cam 48 then comes into contact with a surface of the second cam follower 58 and drives the second cam follower 58, and therefore the second bristle holder 138, back toward the first bristle holder 36.

Figure 4:
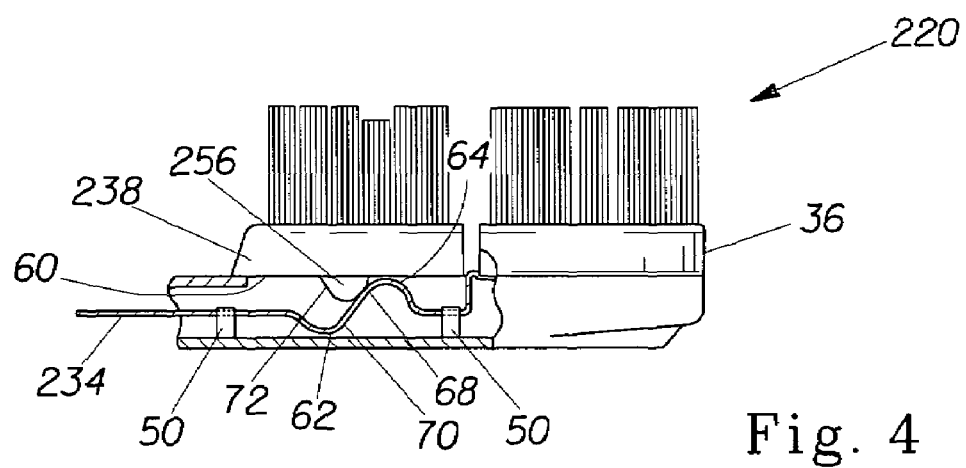
FIG. 4 is an elevational, partial sectional side view of a third embodiment of a stainbrush head suitable for use with the electric stainbrush of FIG. 1, wherein the second bristle holder is shown in a first position.
Figure 5:
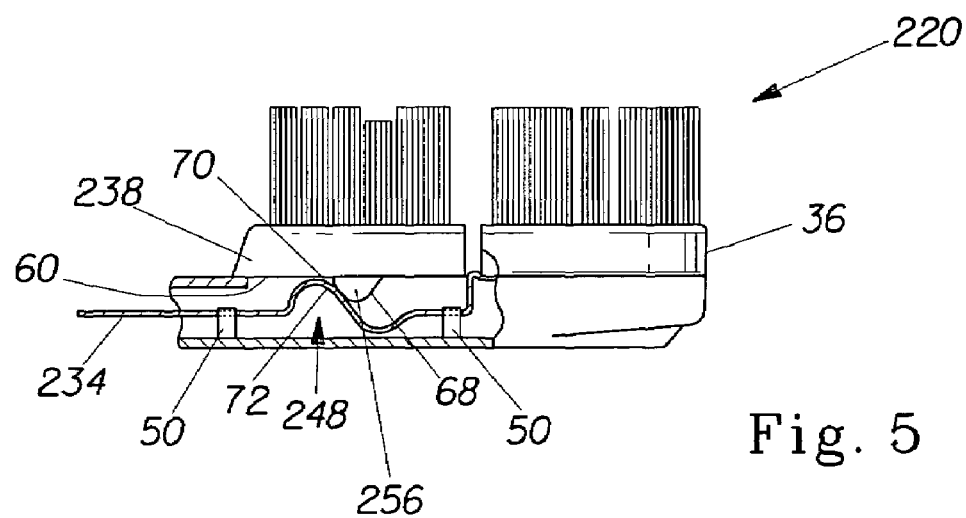
FIG. 5 is an elevational, partial sectional side view of the stainbrush head of FIG. 4, wherein the second bristle holder is shown in a second position.

Referring to FIGS. 4 and 5, a third embodiment of a stainbrush head suitable for use with the electric stainbrush of FIG. 1 will now be described. The head 220 includes a second bristle holder 238 that is slideably mounted in slots (not shown, but the same arrangement as the projection 40 and slot 42 arrangement illustrated in FIG. 2). The second bristle holder 238 is reciprocatingly driven in the same general longitudinal direction as the longitudinal axis of the head 220 and/or shaft 234. A cam 48 included on the shaft 234 operatively interconnects the shaft 234 with second bristle holder 138. Optionally, the shaft 234 can be supported by shaft supports 50. The shaft supports 50 may include C or U shaped portions (not shown) that receive the shaft 234. Other means for retaining the shaft 234 in a support are known in the art. The cam 248 is provided in the form of a plurality of bends 62, 64 in the shaft 234. The bends are sinusoidal or curvilinear in nature in that each bend has one or more adjacent arcuate portions. The bends each have an apex and the apexes are disposed on opposite sides of the shaft 234. A hemispherically-shaped cam follower 256 depends from a bottom surface 60 of the second bristle holder 238 and is disposed between the apexes of the cam 248. As the shaft 234 rotates, a first surface 66 of the cam 248 comes into contact with a first surface 68 of the cam follower 256 and drives the cam follower 256, and therefore the second bristle holder 238, away from the first bristle holder 36 in a longitudinal direction generally the same as the longitudinal axis of the head 220. As the shaft 234 continues to rotate, the forward most apex passes the cam 248 and disengages from the first cam follower surface 68. As shown in FIG. 5, a second surface 70 of the cam 248 then comes into contact with a second surface 72 of the cam follower 256 and drives the cam follower 256, and therefore the second bristle holder 238, back toward the first bristle holder 36. The stroke and frequency of the reciprocating motion of the second bristle holder 410 can be varied by changing the spacing between the apexes and/or the amplitude, shape, or height of the apexes.

Figure 6:
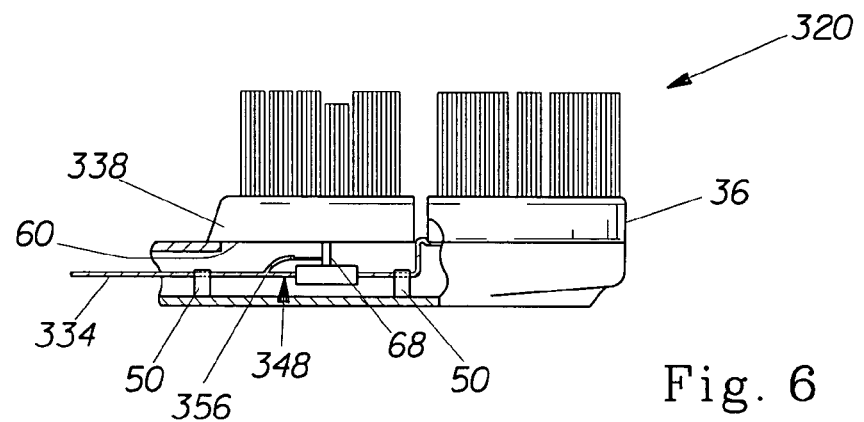
FIG. 6 is an elevational, partial sectional side view of a fourth embodiment of a stainbrush head suitable for use with the electric stainbrush of FIG. 1.
Figure 7:
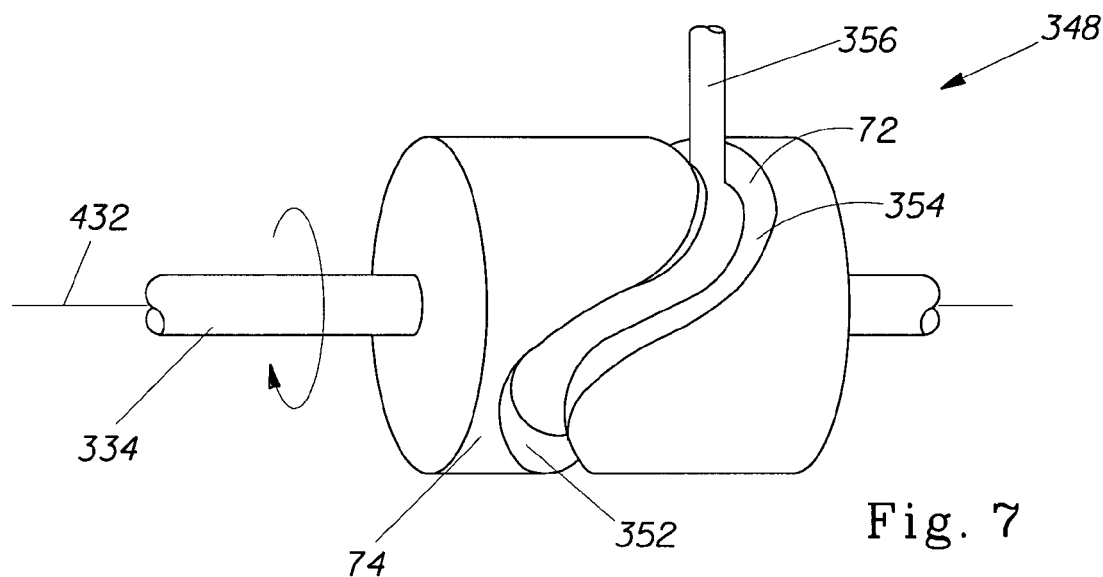
FIG. 7 is a perspective view of a cam suitable for use with the stainbrush head shown in FIG. 6.
Figure 8:
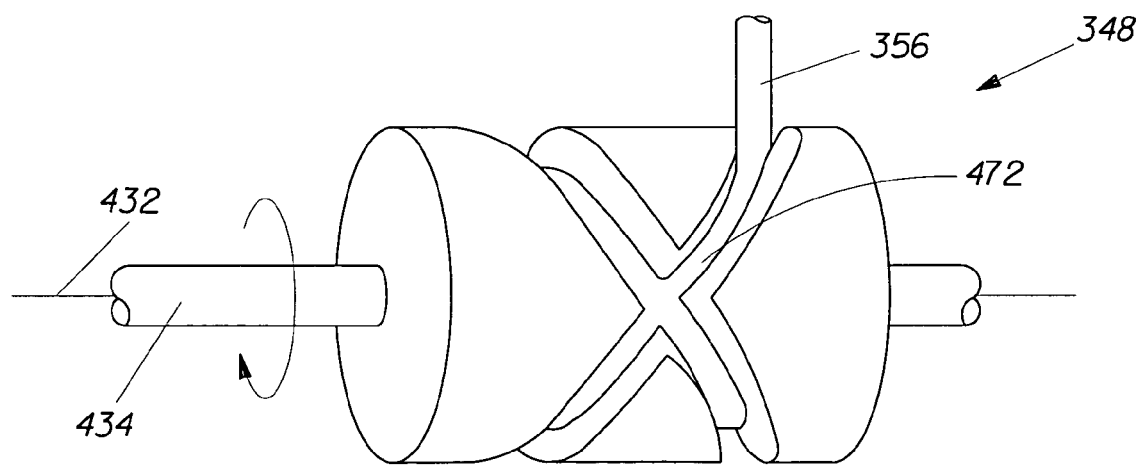
FIG. 8 is a perspective view of another cam suitable for use with the stainbrush head shown in FIG. 6.
Figure 9:
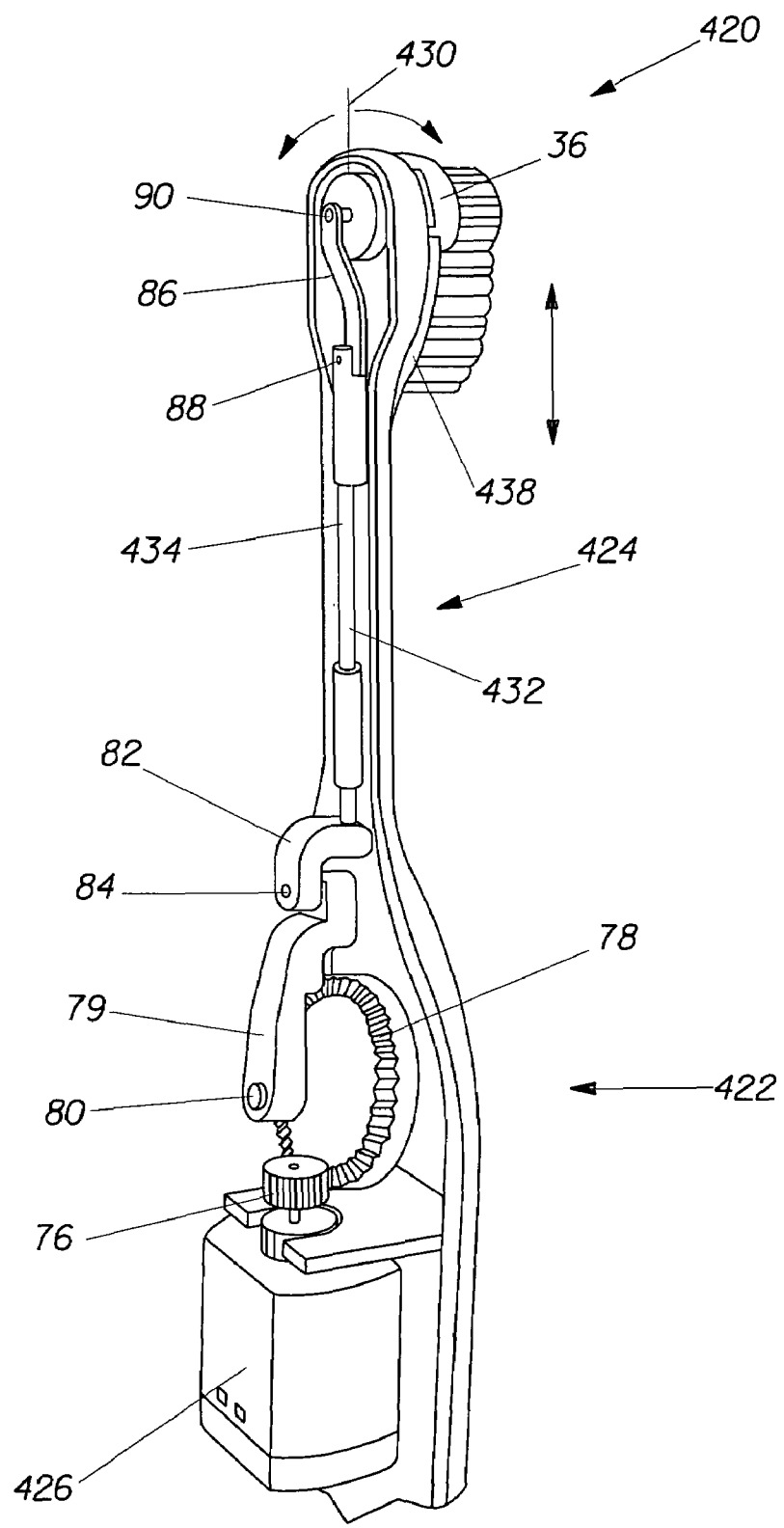
FIG. 9 is a perspective view of an electric stainbrush made in accordance with the present invention, wherein part of the stainbrush housing has been removed in order to illustrate otherwise hidden features and wherein the electric stainbrush incorporates a shaft which reciprocates.

Referring to FIG. 6, a fourth embodiment of a stainbrush head suitable for use with the electric stainbrush of FIG. 1 will now be described. The head 320 includes a second bristle holder 338 that is slideably mounted in slots (not shown, but which can be the same arrangement as the projection 40 and slot 42 arrangement illustrated in FIG. 2). The second bristle holder 338 is reciprocatingly driven in the same general longitudinal direction as the longitudinal axis of the head 320 and/or shaft 334. A cam 348 included on the shaft 134 operatively interconnects the shaft 334 with second bristle holder 338. Optionally, the shaft 334 can be supported by shaft supports 50. The shaft supports 50 may include C or U shaped portions (not shown) that receive the shaft 334. Other means for retaining the shaft 334 in a support are known in the art. The cam 348 is provided in the form of a cylindrically-shaped bead placed or molded over and firmly secured to the shaft 334. As shown in FIGS. 7 and 8, the cam 348 includes a spiral or helical groove 74. The spiral or helical groove 74 extends around the circumference of the bead and spirals about a longitudinal axis of the bead which may, for example, coincide with the longitudinal axis 432 of the shaft 334. The stroke and frequency of the motion imparted to the cam follower 356 by the cam 348 can be varied by changing the shape and dimensions of the groove. For example, the groove 74 of cam 348 is sinusoidal in shape and would provide one complete stroke of the second bristle holder 338 (i.e., one cycle away from and back toward the first bristle holder 36) for one revolution of the shaft 334. FIG. 9 illustrates an alternate cam 348 having a helical groove 472 which is provided in the form of figure eight. This would only provide one-half of a stroke (i.e., only either translation toward or away from the first bristle holder 36) for one revolution of the shaft 334. A cam follower 356 depends from a bottom surface 60 of the second bristle holder 338. The cam follower 356 is slideably received within the groove 72. As the shaft 334 rotates, a first surface 354 of the spiral groove 72, such as a side wall thereof, comes into contact with a first surface of the cam follower 356 and drives the cam follower 356, and therefore the second bristle holder 338, away from the first bristle holder 36 in a longitudinal direction generally the same as the longitudinal axis of the head 320. As the shaft 334 continues to rotate, the cam follower 356 reaches an apex 74 of the spiral groove 72 and the first surface 354 of the spiral groove 72 disengages from the first surface 354 of the groove 72. A second surface 352 of the groove 72, such as the opposite side wall of the groove 72, then comes into contact with a second surface of the cam follower 356 and drives the cam follower 356, and therefore the second bristle holder 338, back toward the first bristle holder 36.

Referring to FIGS. 9 to 13, more exemplary electric stainbrushes made in accordance with the present invention will now be described. These electric stainbrushes utilize a shaft that reciprocates. While these embodiments will be described with respect to the particular motor and shaft arrangement illustrated in FIG. 9 for purposes of simplicity and clarity, it will be appreciated that other motor and reciprocating shaft arrangements can be substituted. For example, U.S. Pat. Nos. 5,226,206; 5,524,312; 5,383,242; 5,465,444; 5,504,959; 5,836,030; 4,845,795; 5,404,608; 5,359,747; and 5,617,601, disclose other motor and reciprocating shaft arrangements that might be suitable. In addition, the electric stainbrush of FIG. 9 might be provided with a replaceable head. A suitable arrangement which can be adapted to the present invention is disclosed in U.S. application Ser. No. 09/850,662, filed May 7, 2001.

Turning to FIG. 9, the electric stainbrush comprises a stainbrush head 420, a body or handle 422, and an elongate neck 424 there between. The drive train, which consists of the shafts and gears that transmit motion from the motor to the first bristle holder 36, is similar to that describe in U.S. Pat. No. 6,178,579. The handle 422 is hollow and includes a motor 426 and batteries (not shown) for powering the motor. A rechargeable power source can be substituted for the batteries. The head 420 has a longitudinal axis 430 passing there through. The longitudinal axis 430 extends in the same general longitudinal direction as a longitudinal axis 432 of a shaft 434. A first bristle holder 36 is disposed at a first end of the head 420, wherein the first end is at the forward most point of the head 420. While the first bristle holder 36 is illustrated as circular in shape, other shapes can be utilized. Further, while the first bristle holder 36 is disposed at the first end of the head 20, it will be appreciated that it can be disposed away from the first end and other features, such as stationary bristles, might be disposed between the first bristle holder 36 and the first end of the head 20. In this embodiment, the first bristle holder only oscillates and does not reciprocate, translate, or perform any other non-rotational or oscillatory motion.

A second bristle holder 438 is disposed adjacent the first bristle holder 436. The second bristle holder reciprocates in the same general longitudinal direction as longitudinal axis 430 of the head 240. In this embodiment, the longitudinal direction of reciprocation is also the same as the longitudinal direction of the longitudinal axis 432 of the shaft 434. While it is desirable to locate the second bristle holder 438 directly adjacent the first bristle holder 36, it is contemplated that a gap may be provided between the first and second bristle holders. In addition, the gap between the first and second bristle holders might be filled with stationary bristles which are embedded in fixed or stationary third bristle holder (not shown) which forms part of the stainbrush head.

A first gear 76 is operatively connected to and powered by the motor 426. A second gear 78 is operatively connected to the first gear 76. The rotational axis of the second gear 78 is approximately normal to the rotational axis of the first gear 76 such that the teeth of the first gear 76 mesh with teeth of the second gear 78, thus causing second gear 78 to rotate as the first gear 76 rotates.

A first arm 79 is eccentrically and pivotably connected to the second gear 76 via a pin 80 or other fastening device. Due to the eccentric connection, the rotational motion of the second gear 76 is converted into a reciprocating motion of the first arm 79. A second arm 82 is pivotably connected to the first arm 78 via a pin 84 or other fastening device. The shaft 434 is fixedly secured, such as by a press fit, to the second arm 82 and to a third arm 86 by a pin 88. The shaft 434 is housed at least partially within the neck 424. The third arm 86 is connected at its terminal end to the first bristle holder 36 via a pin 90 or other fastening device. The terminal end of the third arm 86 is offset from the longitudinal axis of the shaft 434 so that it is pinned adjacent the outer periphery of the first bristle holder 36. This offset arrangement converts the reciprocating motion of the third arm 86 into an oscillating motion of the first bristle holder 36, wherein the first bristle holder 36 oscillates about an axis approximately normal to the axis 434 of the shaft 432.

Figure 10:
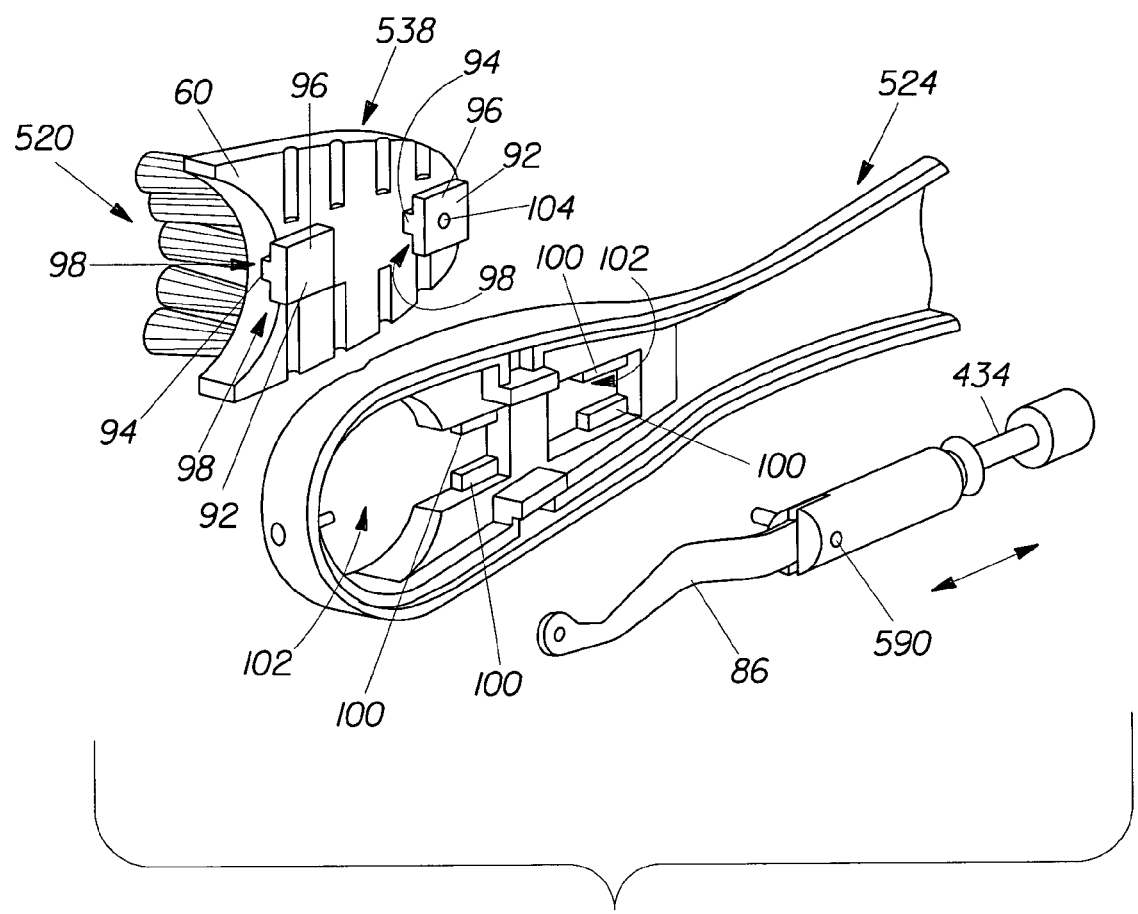
FIG. 10 is an exploded perspective view of a first embodiment of a stainbrush head suitable for use with the electric stainbrush of FIG. 9.

Referring to FIG. 10, a first embodiment of a stainbrush head suitable for use with the electric stainbrush of FIG. 9 will now be described. In the head 520, the pin 590 that interconnects the shaft 434 with the third arm 86 also extends into the second bristle holder 538. The second bristle holder 538 is thereby driven in the same general longitudinal direction as the longitudinal axis of the head 520 and/or the shaft 434. A plurality of T-shaped (in cross section) blocks 92 depend from a bottom surface 60 of the second bristle holder 538. The T-shaped blocks 92 are formed by an upstanding portion 94 which is connected to a transverse portion 96. Slots 98 are formed between the bottom surface 60 of the second bristle holder 538, a side wall of the upstanding portion 94, and an inner side wall of the transverse portion 96. The slots 98 extend in the same general longitudinal direction as the longitudinal axis of head 520. Two pairs of protrusions 100 extend from two cutouts 102 in the housing. The cutouts 102 receive the T-shaped blocks 92. One of the cutouts 102 also has a circular portion which receives the circular shaped first bristle holder (not shown in FIG. 10). The protrusions 100 are slideably received within the slots 98 of the T-shaped blocks 92 when the second bristle holder 538 is installed in the top housing of the head 520. The protrusions 100 and slots 98 cooperate to direct the motion of the second bristle holder 538 in the same general longitudinal direction as the longitudinal axis of the head 520 and/or shaft 534 during use. The rearward most T-shaped block (i.e., the T-shaped block located adjacent the neck) has a hole 104 which receives the pin 590.

As the shaft 434 reciprocates, the pin 590 also reciprocates thereby driving the rearward T-shaped block 92 having the hole 104, and therefore the second bristle holder 538, in a reciprocating longitudinal motion. In addition, the shaft 434 drives the third arm 86 in a reciprocating motion which in turn drives first bristle holder 36 in an oscillating motion, as previously described.

Figure 11:
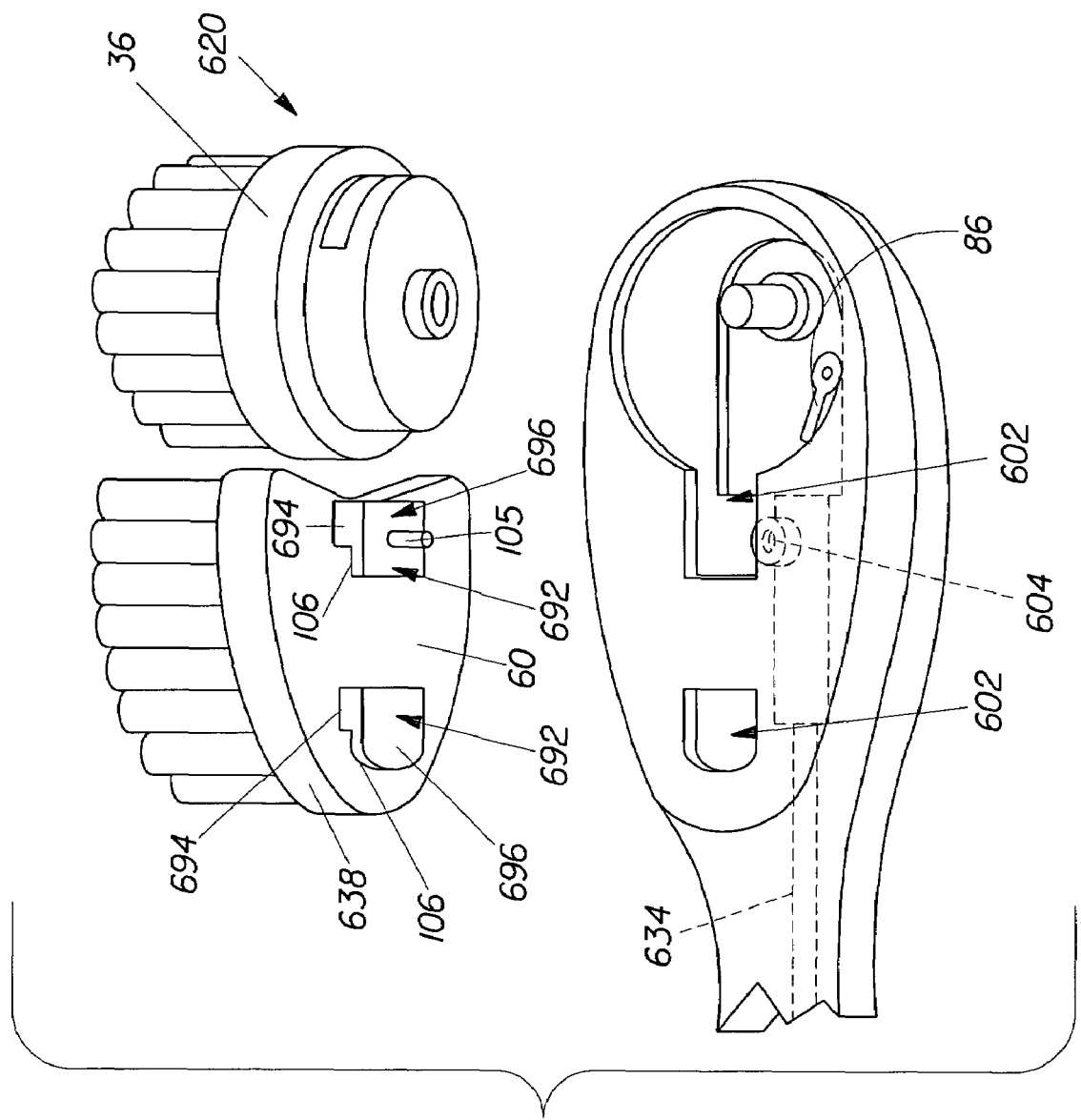
FIG. 11 is an exploded perspective view of a second embodiment of a stainbrush head suitable for use with the electric stainbrush of FIG. 9.

Referring to FIG. 11, a second embodiment of a stainbrush head suitable for use with the electric stainbrush of FIG. 9 will now be described. In the head 620, a second bristle holder 638 is disposed adjacent a first bristle holder 36. The second bristle holder 638 has first and second L-shaped (when viewed from the side) blocks 692 that depend from a bottom surface 60 of the second bristle holder 638. While L-shaped blocks are shown, other shapes can be substituted. The L-shaped blocks 638 are formed from an upstanding portion 694 and a longitudinally directed portion 696 that is aligned in the same direction as the longitudinal axis of the head 620 and/or shaft 634. The L-shaped blocks 692 are received within corresponding slots 602 such that the side walls of the L-shaped blocks 692 and the side walls of the slots 602 cooperate to direct the reciprocating motion of the second bristle holder 638. The underside of a cantilevered portion 106 of the longitudinal portion 696 of the L-shaped blocks 638 engages an inner surface of the stainbrush head housing to retain the second bristle holder 638 with the head 620. The second bristle holder 638 includes a pin 105 which extends from the forward most L-shaped block 692. The pin 105 may be molded and unitary with the L-shaped block 692. The pin 105 is received in a hole 604 associated with the shaft 634 at about the point where the shaft 634 and the third arm 86 are connected. As the shaft 634 reciprocates in the same general direction as the longitudinal axis of the head 620, the pin 105 also reciprocates in generally the same direction, thereby reciprocating the second bristle holder 638 in the same general longitudinal direction as the longitudinal axis of the head 620 and/or shaft 634. The side walls of the slots 602 slidingly engage the side walls of the L-shaped blocks 692, thereby preventing the second bristle holder 638 from moving significantly in a transverse direction. The third arm 86 also drives the first bristle holder 36 in an oscillatory motion as previously discussed with respect earlier embodiments of the present invention.

Figure 12:
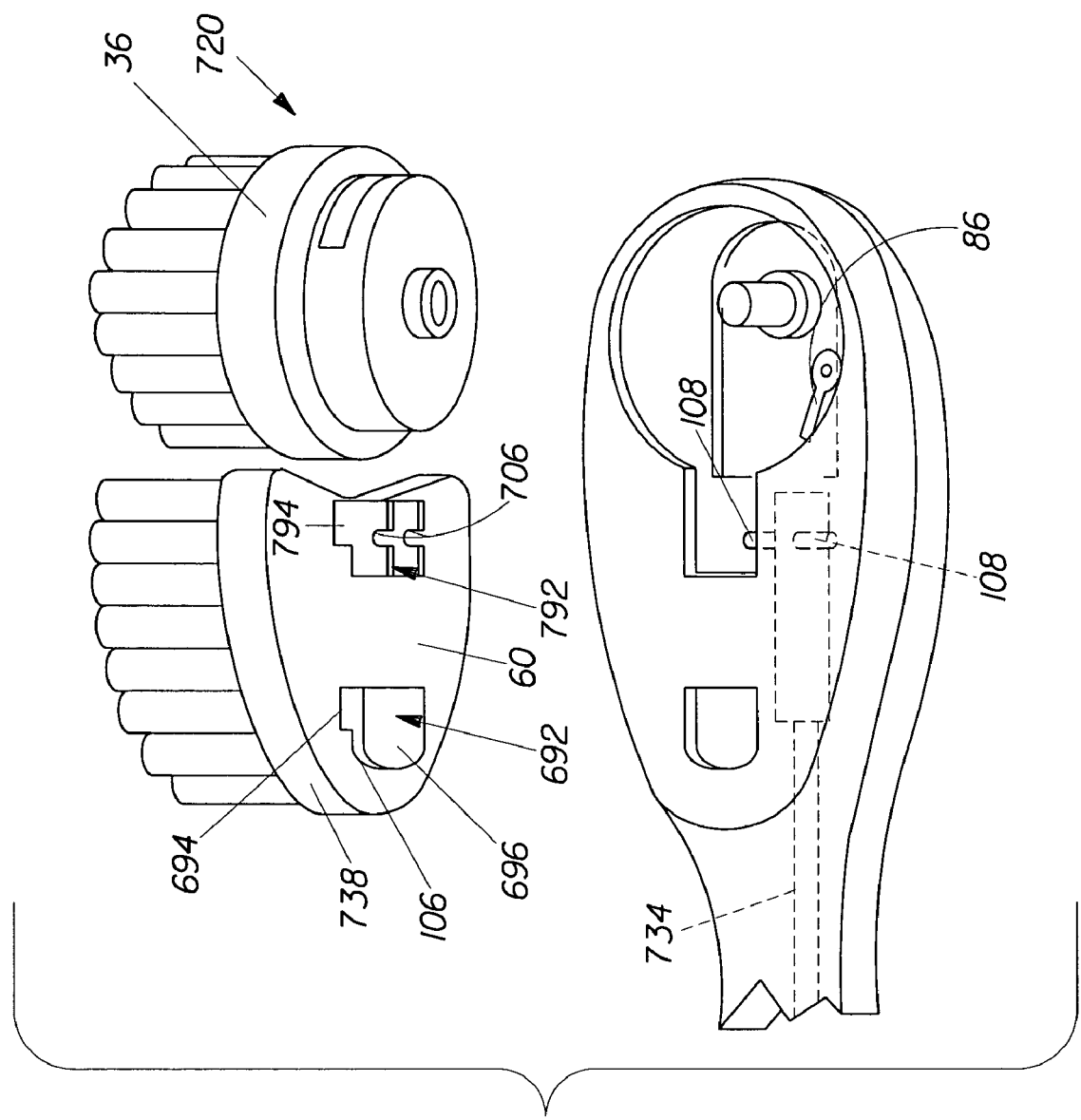
FIG. 12 is an exploded perspective view of a third embodiment of a stainbrush head suitable for use with the electric stainbrush of FIG. 9.

Referring to FIG. 12, a third embodiment of a stainbrush head suitable for use with the electric stainbrush of FIG. 9 will now be described. In the head 720, a second bristle holder 738 is disposed adjacent a first bristle holder 36. The second bristle holder 738 has two L-shaped (in side view) blocks 692 and 792 disposed at the forward and rearward edges of the second bristle holder 738. However T, I or other shaped blocks could also be used. The blocks 692, 792 extend from a bottom surface 60 of the second bristle holder 738. The L-shaped block 692 is the same as previously described for FIG. 11. The L-shaped block 792 has a pair of opposed upstanding portions 794 which each contain a U-shaped slot 706. The U-shaped slots 706 each receive a corresponding pin 108 which extends transversely from the shaft 734. As the shaft 734 reciprocates in the same longitudinal direction as the longitudinal axis of the head 720, the pins 108 also reciprocate, thereby driving the L-shaped blocks 692, 792 and the second bristle holder 738 in the same manner. The third arm 86, which is connected to the shaft 734, drives the first bristle holder 36 in an oscillatory motion as previously.

Figure 13:
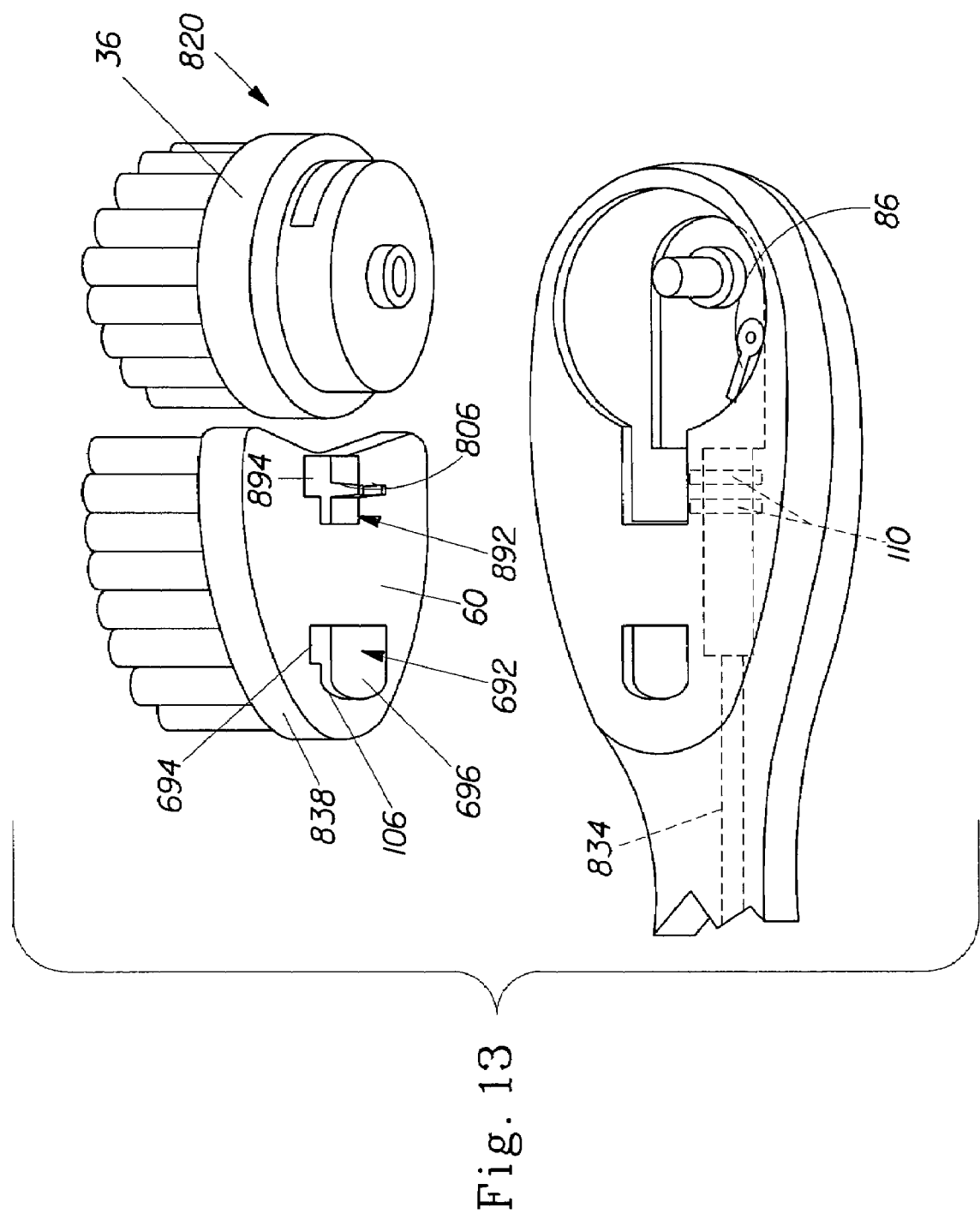
FIG. 13 is an exploded perspective view of a fourth embodiment of a stainbrush head suitable for use with the electric stainbrush of FIG. 9.
Figure 14:
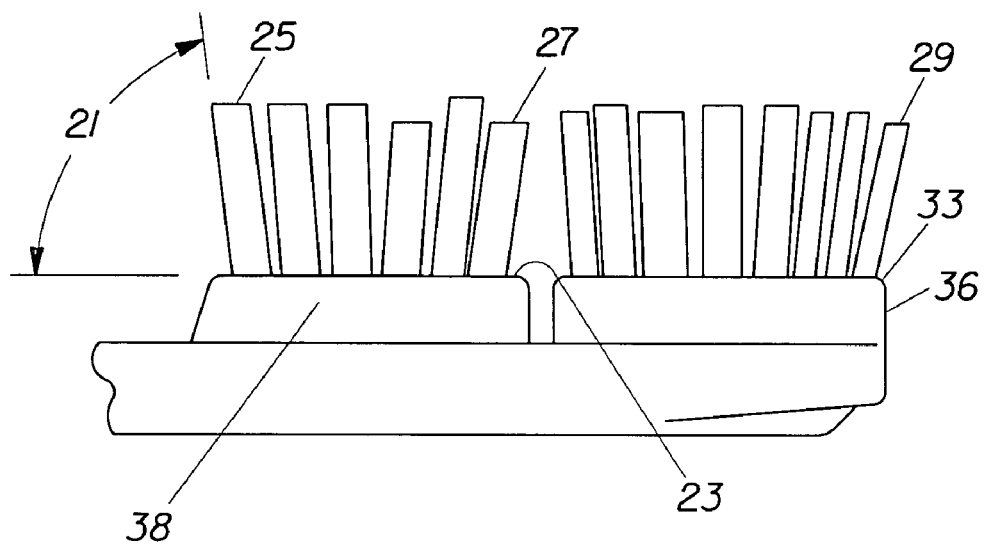
FIG. 14 is a side elevational view of a stainbrush bristle tuft pattern suitable for use with the electric stainbrushes of FIGS. 1 and 9, wherein some of the bristle tufts form an acute angle with the top surface of the bristle holders.
Figure 15:
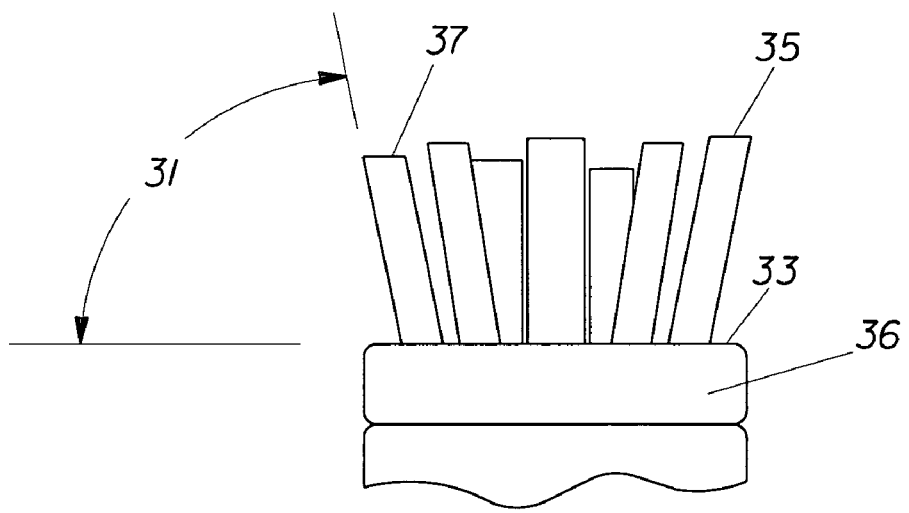
FIG. 15 is a front elevational view of the stainbrush head of FIG. 16.

Referring to FIG. 13, a fourth embodiment of a stainbrush head suitable for use with electric stainbrush of FIG. 9 will now be described. In the head 820, a second bristle holder 838 is disposed adjacent a first bristle holder 36. The second bristle holder 838 has two L-shaped (in side view) blocks 692 and 892 disposed at the forward and rearward edges of the second bristle holder 838. However T, I or other shaped blocks could also be used. The blocks 692, 892 extend from a bottom surface 60 of the second bristle holder 838. The L-shaped block 692 is the same as previously described for FIG. 11. The L-shaped block 892 has an upstanding portion 894 with a C-shaped slot 806 that is sized to slideably receive the shaft 834. A pair of spaced apart rings 110 circumscribe the shaft 834. When assembled, the shaft 834 is received in the C-shaped slot 806 such that the upstanding portion 894 is disposed between the rings 110. As the shaft 834 reciprocates in the same general direction as the longitudinal axis of the head 820, the rings reciprocate the L-shaped block 892 and therefore also the second bristle holder 838 in the same manner. The third arm 86 also drives the first bristle holder 36 in an oscillatory motion as previously discussed. While embodiments of the present invention have been illustrated for simplicity with tufts of bristles that extend in a direction substantially perpendicular to the top surface of the bristle holders, it is contemplated that the bristles might be arranged differently to complement or further enhance the motions of the first and/or second bristle holders. Referring to FIGS. 14 and 15, some or all of the bristles might extend in a direction which forms an acute angle 21 with the top surfaces 23, 33 of the first and second bristle holders 36, 38 and extends in a forward or rearward direction, such as shown by way of example with respect to bristle tufts 25, 27, and 29 respectively. Referring to FIG. 15, in another embodiment, some of the bristles might extend outwardly away from head, in another direction, again forming an acute angle 31 with respect to the top surface 23, 33 of the first and second bristle holders 33, 38, as shown by way of example with respect to bristle tufts 35 and 37. Bristles of varying height might also be used, such as described in U.S. Pat. Nos. Des. 330,286, Des. 434,563. Other preferred bristle arrangements suitable for use include those arrangements described in whole or part in U.S. Pat. Nos. 6,006,394; 4,081,876; 5,046,213; 5,335,389; 5,392,483; 5,446,940; 4,894,880; and international publication no. WO 99/23910.

Figure 16:
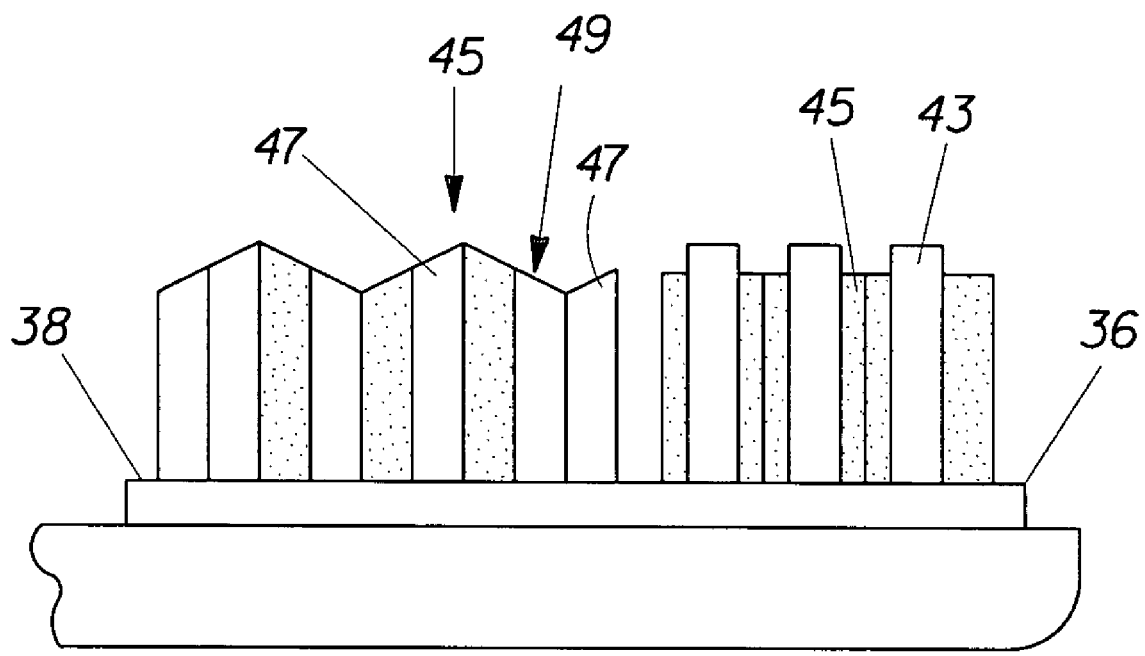
FIG. 16 is a side elevational view of stainbrush bristle tuft pattern suitable for use with the electric stainbrushes of FIGS. 1 and 9.
Figure 17:
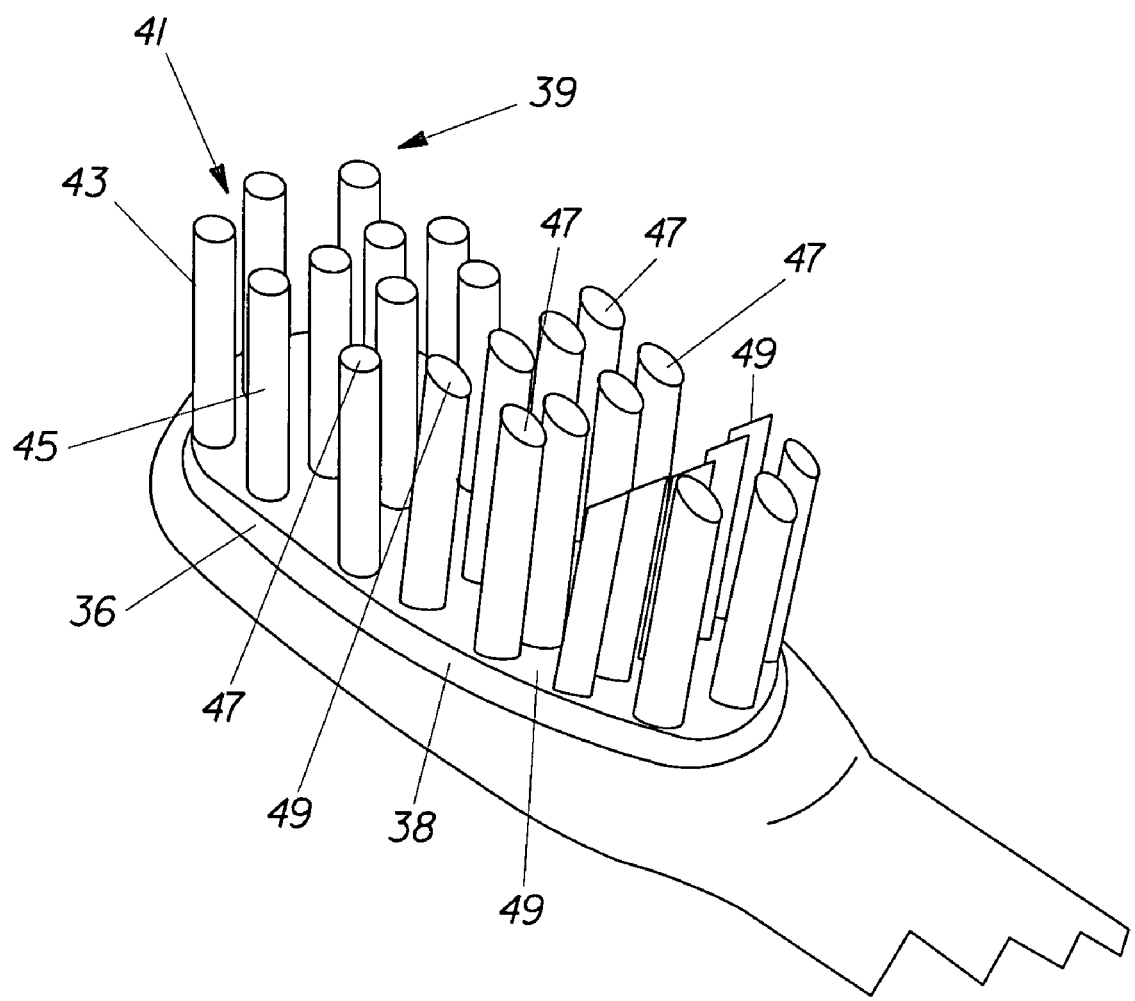
FIG. 17 is a perspective view of the stainbrush head of FIG. 16.
Figure 18:
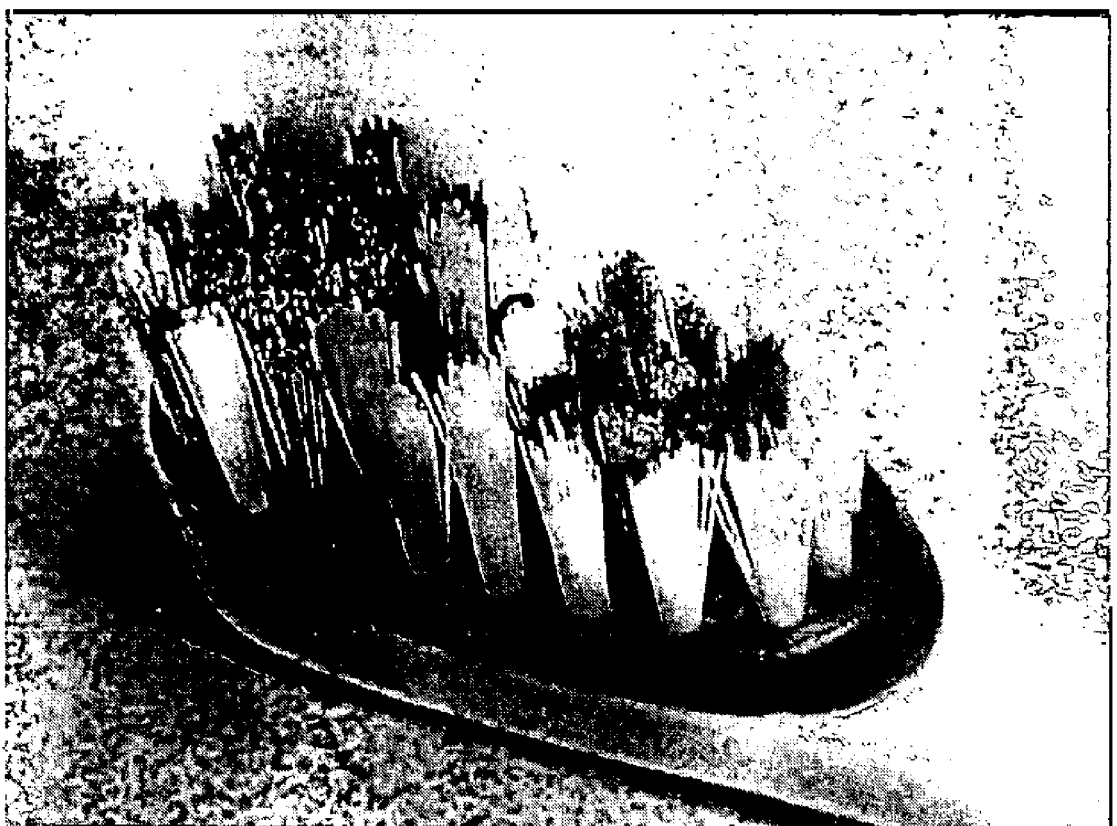
FIG. 18 is a photographic perspective view of the stainbrush head of FIG. 16.
Figure 20:
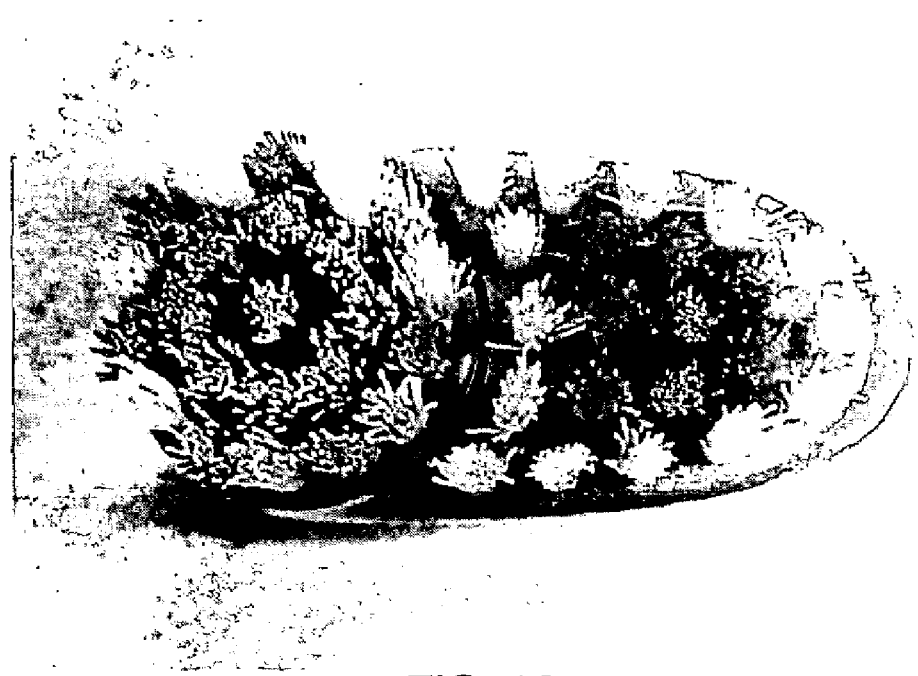
FIG. 20 is a photographic top planar view of the stainbrush head of FIG. 18.
Figure 21:
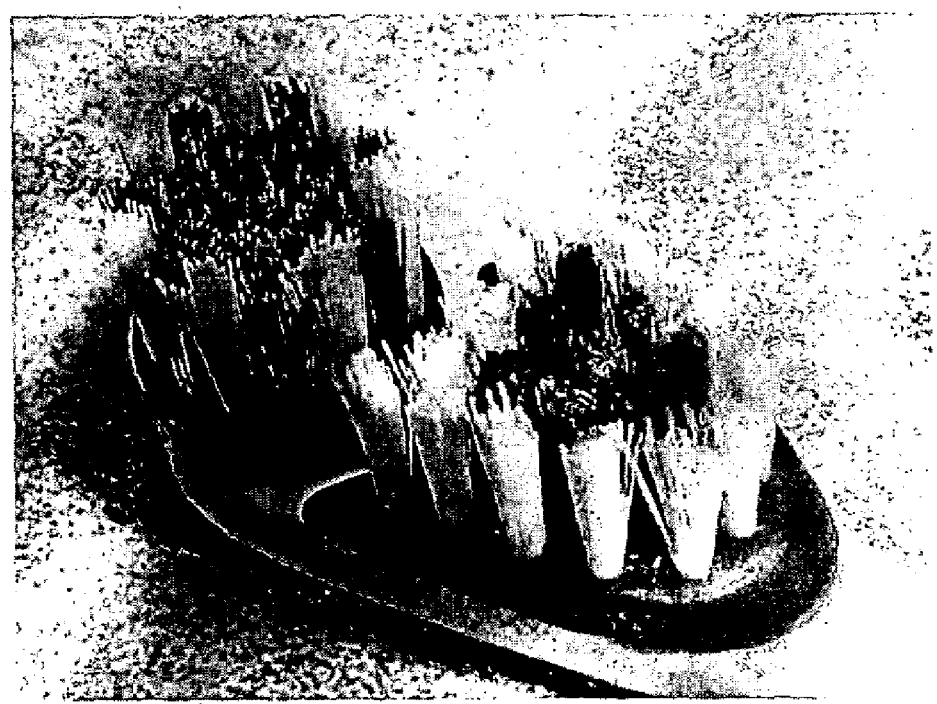
FIG. 21 is a photographic perspective view of a stainbrush head having the bristle pattern of FIG. 16, wherein the second bristle holder is shown in a second position.
Figure 22:
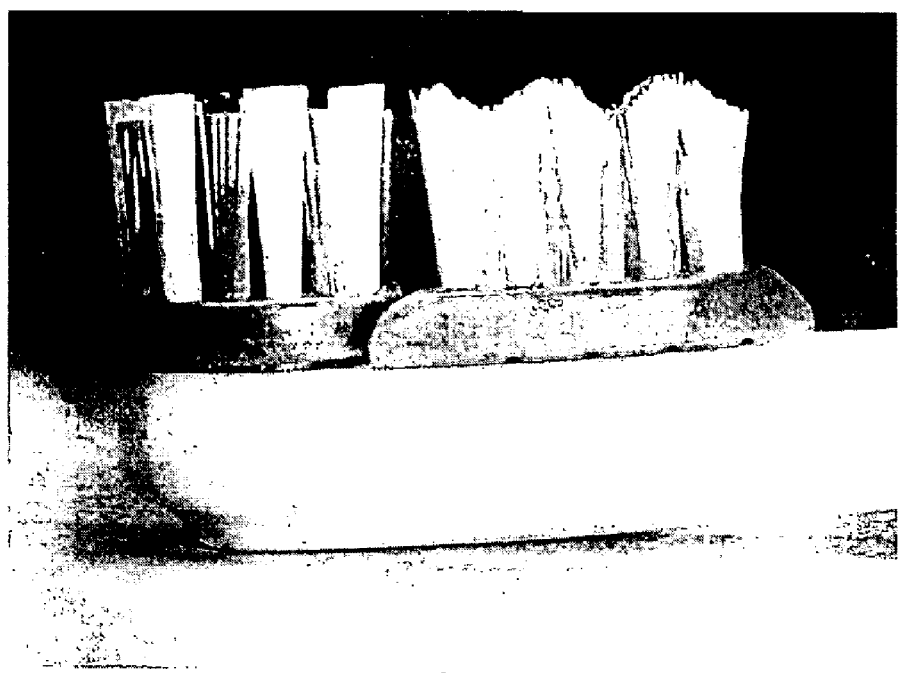
FIG. 22 is a photographic side elevational view of the stainbrush head of FIG. 21.
Figure 23:
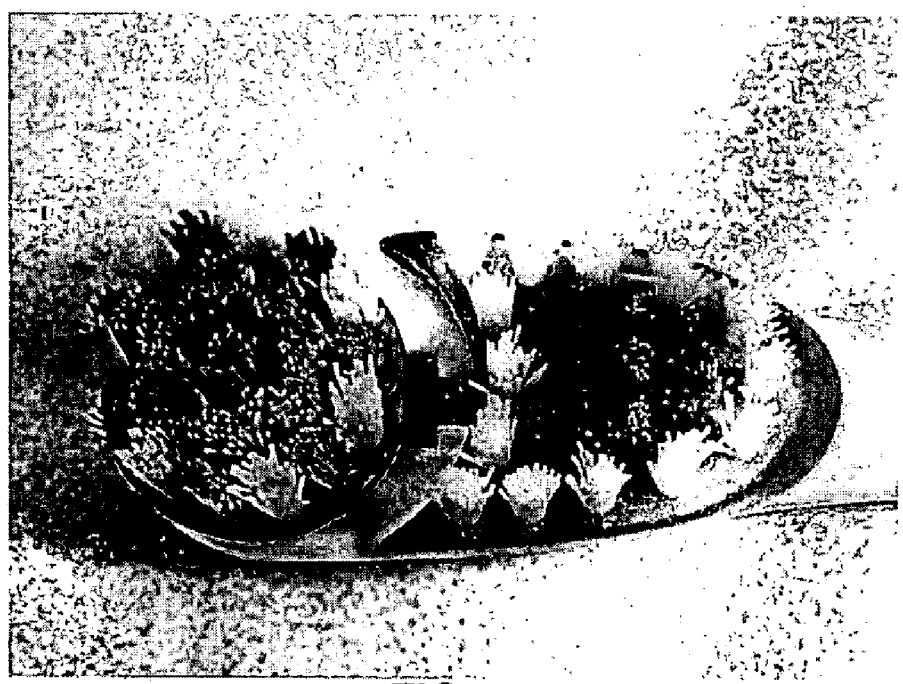
FIG. 23 is a photographic top planar view of the stainbrush head of FIG. 21.
Figure 24:
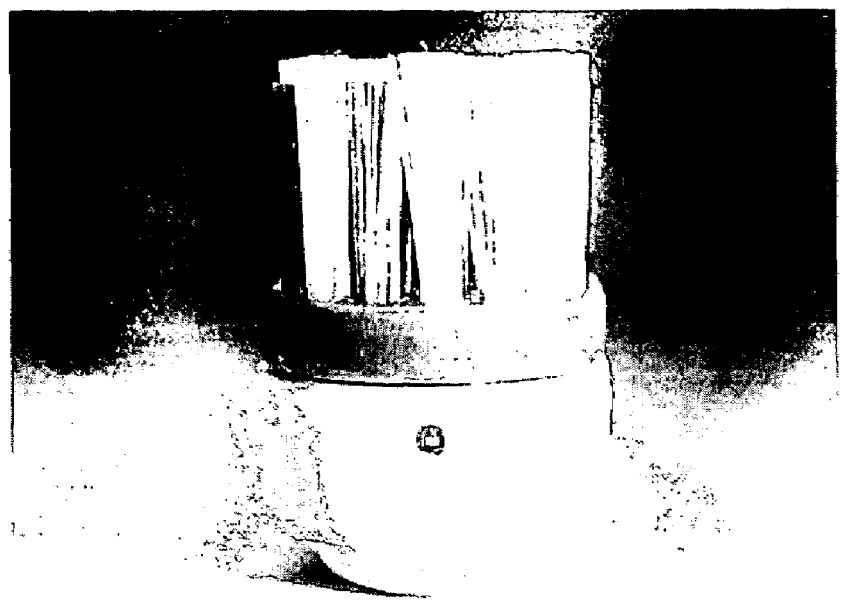
FIG. 24 is a photographic front elevational view of the stainbrush head of FIGS. 18 and 21.
Figure 25:
FIG. 25 is a photographic top planar view of the stainbrush head of FIG. 18 in combination with a handle.
Figure 26:
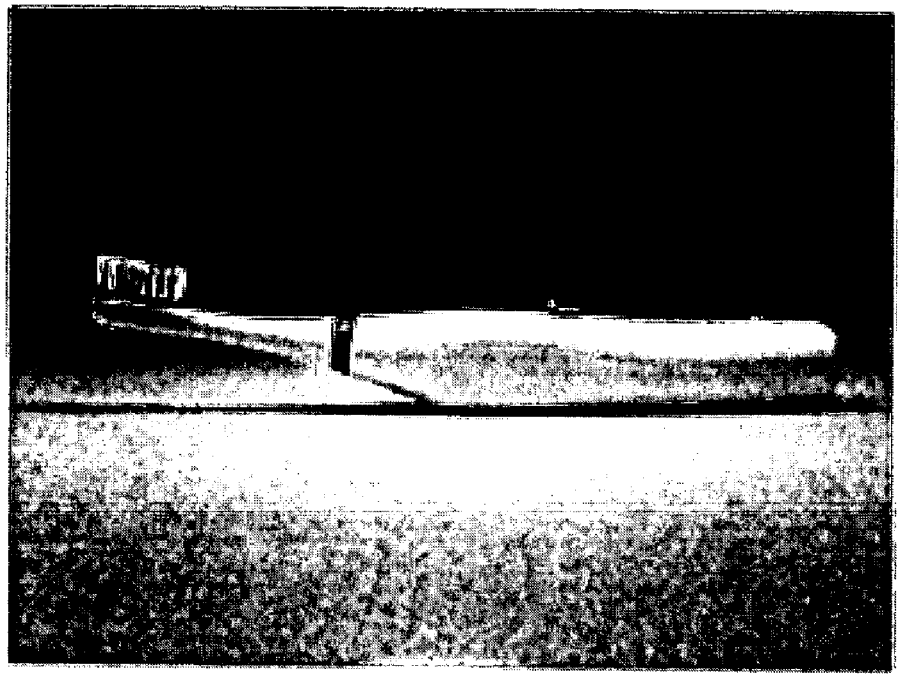
FIG. 26 is a photographic side view of the stainbrush of FIG. 25.
Figure 27:
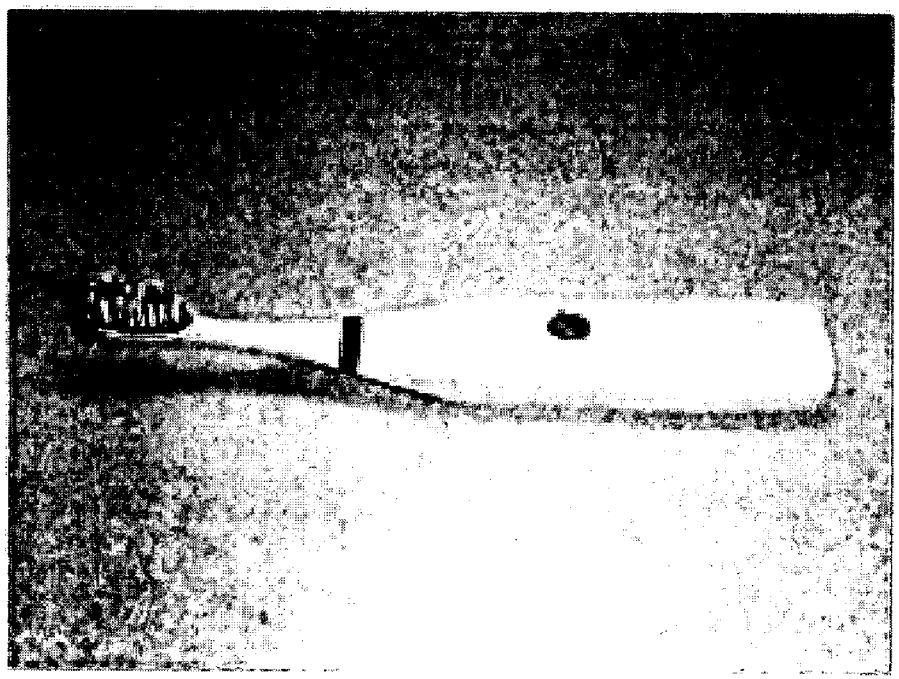
FIG. 27 is a photographic perspective view of the stainbrush of FIG. 25.

While the electric stainbrushes of the present invention can be made with any combination of bristle, dimensions, combinations, angles and arrangements, a preferred arrangement is illustrated in FIGS. 16 and 17. The first bristle holder 36 has two concentric rings of tufts, wherein the outer ring 39 has between 10 and 20 tufts and the inner ring 41 has between 6 and 10 tufts. In one embodiment, the outer ring 39 has 14 tufts and the inner ring 41 has 8 tufts. Between 1 and 2 tufts are disposed inside the inner ring 39 at the center of the first bristle holder. Tufts in the outer ring 39 alternate in height. In one embodiment there are seven tall tufts 43 and seven shorter tufts 45. The difference in length between the tall tufts 43 and the shorter tufts 45 is between about 0.5 mm and about 2.5 mm in one embodiment and between about 1 mm and about 2 mm in other embodiment.

The bristles can be provided with different characteristics, such as different heights (tall and short) as shown; and soft or firm. For example, soft bristles may be preferred for cleaning delicate fabrics (e.g., silk garments) and delicate hard surfaces (e.g., glass, plexiglass, compact discs, DVDs, gold plated surfaces, etc.). Alternatively, firmer bristles may be preferred for more rugged fabrics (e.g., denim, canvas, nylon, etc.) and most hard surfaces. Additionally, stiffer bristles typically require less force to be applied by the user, versus softer bristles. Less force applied by the user results in overall less stress on the user's fingers, hands, wrist arm and/or shoulder.

The first bristle holder 36 oscillates (i.e., the angle of rotation) between about 20 degrees and about 45 degrees in one embodiment and between about 25 degrees and about 35 degrees in another embodiment. The first bristle holder has a peak oscillation frequency between about 6,000 and about 10,000 cycles per minute in one embodiment and between about 7,000 and 9,000 cycles per minute in another embodiment. A cycle is one complete clockwise and counterclockwise rotation (or vice versa) when the batteries are fully charged. It is contemplated that the oscillation frequency may drop outside of these ranges as the batteries are drained by use. Since the same shaft is driving both the first and second bristle holders, the second bristle holder would also have the same frequency of operation. A cycle for the second bristle holder is one complete stroke toward the handle and one complete stroke back toward the first bristle holder (or vice versa).

The second bristle holder 38 has between 15 and 40 tufts in one embodiment and between about 20 and about 30 tufts in another. The tufts are arranged in between about 5 and about 15 rows, as best seen in FIG. 16. The rows may be linear or curvilinear. The tips of the tufts of bristles are provided with a linear, wave-like profile when viewed from the side, as best seen in FIG. 16, although this profile can be more curvilinear. This arrangement has between 2 and about 8 peaks 45 in one embodiment and between about 3 and about 6 peaks 45 in another embodiment, when viewed from the side. The peaks 45 are formed by adjacent tufts that have oppositely angled tuft end surfaces 47 and 49. The same is true for the valleys 51. The distance from peak-to-peak is between about 2 mm and about 10 mm in one embodiment and between about 4 mm and about 6 mm in another embodiment. The depth from peak-to-valley is between about 0.5 mm and about 3 mm in one embodiment and between about 1 mm and about 2 mm in another embodiment. Each tuft is cut at about 45 degrees. The tuft arrangement of the second bristle holder 38 has a length between about 5 mm and about 20 mm and a width between about 5 mm and 15 mm in one embodiment and a length between about 10 mm and about 15 mm and a width between about 10 mm and 15 mm in another embodiment. The tuft pattern of the second bristle holder 38 tapers toward the longitudinal axis of the stainbrush head as the taper progresses rearward. The second bristle holder has a stroke (i.e., a displacement in one direction) between about 1 mm and about 6 mm in one embodiment and a stroke between about 2 mm and about 4 mm in another embodiment.

The stainbrush aspect of the invention has been described with reference to particular embodiments. Modifications and alterations will occur to others upon reading and understanding this specification. For example, while certain cams have been described as comprising bends in a shaft and other cams have been described as including appropriately shaped beads secured to a shaft, the cams are not limited to the suggested form. Indeed, bends may be substituted for beads and beads may be substituted for bends and other shapes, sizes, and configurations can be implemented. It is intended that all such modifications and alterations are included insofar as they come within the scope of the appended claims or equivalents thereof.

B. Method of Use

The present invention also encompasses a method of using the stainbrush to clean inanimate surfaces. In a preferred embodiment, the method comprises a) having the electric stainbrush of the present invention, b) putting a solution such as an aqueous solution, a lipophilic fluid or a combination thereof in contact with an inanimate surface; and c) employing the electric stainbrush to brush solution on the inanimate surface.

The brush of the present invention is particularly useful for cleaning inanimate surfaces. For example, the stainbrush can be used alone or with additional laundry and stain pretreatment products (including liquid and powder detergents, bleach, water, specialty pretreaters) to clean and remove stains from fabrics, particularly wearable fabrics. Fabrics include acrylic, cotton, lycra, polyester, rayon, spandex, washable silks with colorfast qualities, and wool, along with any blends of the above materials. The stainbrush can be used to apply product directly to the surface of the stain on the fabric via the bristles, or products can be directly applied to the stained fabric prior to using the device. Once the stain has been prepared and the operator has enabled the brush head to rotate by actuating the power button, the stainbrush can be used to manually brush the surface of the stain on the fabric in any direction (circular, vertical, horizontal, diagonal, or any combination of the above). The stainbrush can also be used when not actuated in the same manner as above.

Additional uses for the stainbrush include cleaning household fabrics such as upholstery, carpets, bedding, curtains, throw rugs, tablecloths, and other non-wearable fabrics in the same manner as listed above.

The stainbrush can also be used to clean inanimate hard surfaces, including those commonly found in a household (e.g., countertops, bathroom appliances, dishes, faucets, fixtures, floor baseboards, grout, kitchen appliances, shower doors, sinks, tile, toilets, tools, and tubs), shoe cleaning and polishing, car features (upholstery, cup holders, trim, detailing, car wheels, spokes) and jewelry.

Preferred hard surfaces include enamel surfaces. Herein, "enamel surface" means an inanimate surface being made of or coated with enamel. Herein "enamel" means titanium or zirconium white enamel or titanium or zirconium white powder enamel used as a coating for metal (e.g., steel) surfaces preferably to prevent corrosion of said metal surfaces. Enamel surfaces can typically be found in houses: e.g., in bathrooms or in kitchens, and include, e.g., bathrooms, fixtures and fittings sinks, showers, shower wash basins, tiles, tubs, and the like. Furthermore, cookware, dishes and the like may have an enamel surface. Enamel surfaces may also be found on household appliances which may be coated with enamel on their inside and/or outside surface including, but not limited to, automatic dryers, freezers, heating boiler, microwave ovens, conventional ovens, dishwashers refrigerators, washing machines, and so on. Further enamel surfaces may be found in industrial, architectural and the like applications. Examples of enamel surfaces found in said applications include enamel surfaces on or in architectural panels, chemical processing equipment, heat exchangers, hot water tanks, mechanical equipment, pipelines, pumps, reaction vessels, signs, silos, or tanks.

C. Self-Instructing Article of Commerce

The present invention also encompasses articles of commerce comprising 1) the electric stainbrush of the present invention, and 2) a set of instructions directing the user in the method of the present invention for cleaning an inanimate surface.

In a preferred embodiment, the article of commerce comprises the stainbrush of the present invention in association with a set of instructions, wherein the instructions direct the user to follow the method of cleaning an inanimate surface described above. For example, in one embodiment, such instructions would direct the user to 1) put an aqueous solution in contact with the inanimate surface to be cleaned, and 2) employ the electric stainbrush to brush the aqueous solution on the inanimate surface.

Herein, "in association with", when referring to such instructions, means the instructions are either directly printed on the stainbrush; directly printed on the packaging for the stainbrush; printed on a label attached to the stainbrush; printed on a label attached to the packaging for the stainbrush; or presented in a different manner including, but not limited to, a brochure, print advertisement, electronic advertisement, broadcast or internet advertisements, and/or other media, so as to communicate the set of instructions to a consumer of the stainbrush.

D. Cleaning Solution

The cleaning solution of the present invention may be an aqueous solution, a lipophilic fluid, or a combination thereof.

1. Aqueous Solution

As used herein, "aqueous solution" refers to a solution which contains water. The aqueous solution employed in the present invention may be any solution that facilitates the removal of a stain on an inanimate surface. In one embodiment, the aqueous solution comprises at least about 10% water. In another embodiment the aqueous solution further comprises a surfactant.

Preferably, in embodiments involving the cleaning of fabrics, the aqueous solution is a liquid laundry detergent. In another embodiment for cleaning fabrics, the user may combine a granular laundry detergent with water to form a suitable aqueous solution.

Preferably, in embodiments involving the cleaning of hard surfaces, the aqueous solution is a liquid hard surface cleaner. In another embodiment for cleaning hard surfaces, the user may combine a granular hard surface cleaner with water to form a suitable aqueous solution.

In another embodiment, the aqueous solution further comprises a solvent. Solvents are particularly useful when cleaning a hard surface.

Additional non-limiting examples of aqueous solutions for use in the present invention may further comprise: ammonia, all-purpose cleaners, baking soda, bathroom/shower cleaners, bleach, car cleaners, and/or carpet cleaners.

In another embodiment, the aqueous solution further comprises particles. Such particles are particularly useful in facilitating mechanical disruption of a stain on the inanimate surface.

2. Lipophilic Fluid

The lipophilic fluid employed in the present invention may be any non-aqueous fluid that facilitates the removal of a stain on an inanimate surface and meets the requirements set forth in the Lipophilic Fluid Test (LF Test) as described below.

Qualification of Lipophilic Fluid—Lipophilic Fluid Test (LF Test)

Any non-aqueous fluid that is both capable of meeting the Lipophilic Fluid Test and that is at least partially liquid and/or readily flowable (nonviscous) at ambient temperature and pressure is suitable as a lipophilic fluid herein. In general, a suitable lipophilic fluid can be fully liquid at ambient temperature and pressure, can be an easily melted solid (i.e.; a non-limiting example of which is one that becomes liquid at temperatures in the range from about 0° C. to about 60° C.), or can comprise a mixture of liquid and vapor phases at ambient temperatures and pressures (e.g.; at 25° C. and 1 atm. pressure). The Lipophilic Fluid Test, which may be used to assist with the identification of suitable lipophilic fluids for use in the present invention, relates to the ability of a particular material to remove sebum.

The test method uses commercially available Crisco® canola oil, oleic acid (95% pure, available from Sigma Aldrich Co.) and squalene (99% pure, available from J. T. Baker) as model soils for sebum. The test materials should be substantially anhydrous and free from any added adjuncts, or other materials. As a general guideline, perfluorobutylamine (Fluorinert FC-43®, available from 3M Corporation) on its own (with or without adjuncts) is a reference material that, by definition, is unsuitable as the lipophilic fluid while cyclopentasiloxane (D5) dissolves sebum.

Prepare three vials. Place 1.0 g of canola oil in the first; in a second vial place 1.0 g of the oleic acid (95%), and in a third and final vial place 1.0 g of the squalene (99%). Add 1 g of the fluid to be tested for lipophilicity to each vial. Separately mix at room temperature and pressure each prepared vial for 20 seconds on a standard vortex mixer at maximum setting. Place vials on the bench and allow to stand for 15 minutes at room temperature and pressure. If, after 15 minutes a single phase is formed in any of the vials containing lipophilic soils, then the fluid qualifies as suitable for use as a "lipophilic fluid" in accordance with the invention. However, if two or more separate layers are formed in all three vials, then the amount of fluid dissolved in the oil phase will need to be further determined before rejecting or accepting the fluid as qualified as a "lipophilic fluid."

In such a case, with a syringe, carefully extract a 200 microliter sample from each layer in each vial. The syringe-extracted layer samples are placed in GC autosampler vials and subjected to conventional GC analysis after determining the retention time of calibration samples of each of the three models soils and the fluid being tested. If more than 1% of the test fluid by GC, preferably more, is found to be present in any one of the layers which consists of the oleic acid, canola oil or squalene layer, then the test fluid is also qualified for use as a lipophilic fluid. If needed, the method can be further calibrated using perfluorobutylamine, i.e., Fluorinert FC-43® (fail) and cyclopentasiloxane (pass).

A suitable GC is a Hewlett Packard Gas Chromatograph HP5890 Series II equipped with a split/splitless injector and FID. A suitable column used in determining the amount of lipophilic fluid present is a J&W Scientific capillary column DB-1HT, 30 meter, 0.25 mm id, 0.1 um film thickness cat# 1221131. The GC is suitably operated under the following conditions:

Carrier Gas: Hydrogen; Column Head Pressure: 9 psi; Flows: Column Flow @ ~1.5 ml/min.; Split Vent @ ~250-500 ml/min.; Septum Purge @ 1 ml/min.; Injection: HP 7673 Autosampler, 10 ul syringe, 1 ul injection; Injector Temperature: 350° C.; Detector Temperature: 380° C.; Oven Temperature Program: initial 60° C., hold 1 min.; rate 25° C./min.; final 380° C. hold 30 min.

Preferred lipophilic fluids suitable for use herein can further be qualified for use on the basis of having an excellent garment care profile. Garment care profile testing is well known in the art and involves testing a fluid to be qualified using a wide range of garment or fabric article components, including fabrics, threads and elastics used in seams, etc., and a range of buttons. Preferred lipophilic fluids for use herein have an excellent garment care profile, for example they have a good shrinkage or fabric puckering profile and do not appreciably damage plastic buttons.

For purposes of garment care testing or other qualification, e.g., flammability, a lipophilic fluid for use in the lipophilic fluid can be present in a mixture, e.g., with water, at approximately the ratio to be used in the final lipophilic fluid which will come into contact with fabric articles. Certain materials, which remove sebum, qualify for use as lipophilic fluids; for example, ethyl lactates can be quite objectionable in their tendency to dissolve buttons, and if such a material is to be used in the lipophilic fluid, it will be formulated with water and/or other solvents such that the overall mix is not substantially damaging to buttons. Other lipophilic fluids, D5 for example, meet the garment care requirements commendably. Some suitable lipophilic fluids may be found in granted U.S. Pat. Nos. 5,865,852; 5,942,007; 6,042,617; 6,042,618; 6,056,789; 6,059,845; and 6,063,135.

"Siloxane" as used herein means silicone fluids which are non-polar and insoluble in water or lower alcohols. Linear siloxanes (see for example U.S. Pat. Nos. 5,443,747, and 5,977,040) and cyclic siloxanes are useful herein, including the cyclic siloxanes selected from the group consisting of octamethyl-cyclotetrasiloxane (tetramer), dodecamethyl-cyclohexasiloxane (hexamer), and preferably decamethyl-cyclopentasiloxane (pentamer, commonly referred to as "D5"). A preferred siloxane comprises more than about 50% cyclic siloxane pentamer, more preferably more than about 75% cyclic siloxane pentamer, most preferably at least about 90% of the cyclic siloxane pentamer. Also preferred for use herein are siloxanes which are a mixture of cyclic siloxanes having at least about 90% (preferably at least about 95%) pentamer and less than about 10% (preferably less than about 5%) tetramer and/or hexamer.

Mixtures of lipophilic fluid are also suitable, and provided that the requirements of the Lipophilic Fluid Test, as described below, are met.

Other suitable lipophilic fluids include, but are not limited to, diol solvent systems e.g., higher diols such as C6 or C8 or higher diols, organosilicone solvents including both cyclic and acyclic types, and the like, and mixtures thereof.

Nonlimiting examples of low volatility nonfluorinated organic solvents include for example OLEAN® and other polyol esters, or certain relatively nonvolatile biodegradable mid-chain branched petroleum fractions.

Nonlimiting examples of glycol ethers include propylene glycol methyl ether, propylene glycol n-propyl ether, propylene glycol t-butyl ether, propylene glycol n-butyl ether, dipropylene glycol methyl ether, dipropylene glycol n-propyl ether, dipropylene glycol t-butyl ether, dipropylene glycol n-butyl ether, tripropylene glycol methyl ether, tripropylene glycol n-propyl ether, tripropylene glycol t-butyl ether, tripropylene glycol n-butyl ether.

Nonlimiting examples of other silicone solvents, in addition to the siloxanes, are well known in the literature, see, for example, Kirk Othmer's Encyclopedia of Chemical Technology, and are available from a number of commercial sources, including GE Silicones, Toshiba Silicone, Bayer, and Dow Corning. For example, one suitable silicone solvent is SF-1528 available from GE Silicones.

Nonlimiting examples of glycerine derivative solvents include materials having the following structure:

Nonlimiting examples of suitable glycerine derivative solvents for use in the methods and/or apparatuses of the present invention include glyercine derivatives having the following structure:

Structure I

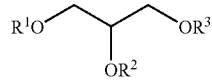

wherein $R^1$, $R^2$ and $R^3$ are each independently selected from: H; branched or linear, substituted or unsubstituted $C_1$-$C_{30}$ alkyl, $C_2$-$C_{30}$ alkenyl, $C_1$-$C_{30}$ alkoxycarbonyl, $C_3$-$C_{30}$ alkyleneoxyalkyl, $C_1$-$C_{30}$ acyloxy, $C_7$-$C_{30}$ alkylenearyl; $C_4$-$C_{30}$ cycloalkyl; $C_6$-$C_{30}$ aryl; and mixtures thereof. Two more of $R^1$, $R^2$ and $R^3$ together can form a $C_3$-$C_8$ aromatic or non-aromatic, heterocyclic or non-heterocyclic ring.

Nonlimiting examples of suitable glycerine derivative solvents include 2,3-bis(1,1-dimethylethoxy)-1-propanol; 2,3-dimethoxy-1-propanol; 3-methoxy-2-cyclopentoxy-1-propanol; 3-methoxy-1-cyclopentoxy-2-propanol; carbonic acid (2-hydroxy-1-methoxymethyl)ethyl ester methyl ester; glycerol carbonate and mixtures thereof.

Nonlimiting examples of other solvents include lipophilic fluids that have an ozone formation potential of from about 0 to about 0.31, lipophilic fluids that have a vapor pressure of from about 0 to about 0.1 mm Hg, and/or lipophilic fluids that have a vapor pressure of greater than 0.1 mm Hg, but have an ozone formation potential of from about 0 to about 0.31. Nonlimiting examples of such lipophilic fluids that have not previously been described above include carbonate solvents (i.e., methyl carbonates, ethyl carbonates, ethylene carbonates, propylene carbonates, glycerine carbonates) and/or succinate solvents (i.e., dimethyl succinates).

E. Absorbent Stain Receiver Article

In another embodiment, the stain-removal brush and cleaning solution are used in combination with an Absorbent Stain Receiver Article ("ASRA")—The ASRA herein can comprise any of a number of absorbent structures which provide a capillary pressure difference through their thickness (Z-direction). The ASRA is especially useful when removing stains from fabric. Liquid held in the fabric may be removed by contacting it with another absorbent structure such as the ASRA, herein. In this process, liquid is transferred from the capillaries of the fabric to the capillaries of the ASRA.

Liquid is held in capillaries by capillary pressure. Capillary pressure (Pc) is generally described by the following equation:

$$Pc = (2 \times G \times \cos A)/R$$

where

G = the surface tension of the liquid
A = the contact angle between the liquid and the capillary wall
R = the radius of the capillary Accordingly, capillary pressure is highest in capillaries which have a low contact angle and a small radius. Liquid is held most tightly by high capillary pressure and will move from areas of low capillary pressure to areas of high capillary pressure. Hence, in the subject ASRA which provides a capillary pressure difference through its thickness, liquid will move from low capillary pressure areas to high capillary pressure areas. Capillary pressure can be measured using a variety of techniques, but will employ the liquid cleaning composition as the test liquid.

In reality, most absorbent materials are complex structures comprised of a range of capillary sizes and contact angles. For this discussion, the capillary pressure of a material or capillary pressure zone within a material is defined as the volumetric weighted average of the range of pressures found within that material or zone.

For purposes of illustration, in circumstances wherein a soiled fabric saturated with cleaning solution is in liquid communication contact with two stacked, identical layers of homogeneous absorbent material, such as a paper towel, solution and soil would readily transfer from the fabric to the towel until the capillary pressure is approximately equal in the two materials. At equilibrium a certain amount of solution and soil will remain in the fabric. The exact amount will depend on the basis weight and capillary pressure characteristics of the fabric and towel. A reduced amount of residual solution and soil in the fabric, and therefore better cleaning, would result from replacing the bottom layer (layer not in direct contact with the fabric) of towel with an absorbent layer of capillary pressure higher than that of the towel. By virtue of its higher capillary pressure this absorbent layer will cause more solution to transfer from the low capillary pressure top towel layer to the high capillary pressure absorbent layer which in turn causes more solution to transfer from the fabric to the top towel layer. The result is better cleaning due to less residual solution and soil remaining in the fabric.

This type of multi-layer system is also beneficial when Z-directional pressure is applied to the wetted stained fabric and ASRA. This pressure compresses the various materials, thereby lowering their void volume and liquid absorption capacity (increasing the % saturation of the materials). This can cause liquid to be squeezed out. The layered structure allows for free liquid to be absorbed by the lower layer, i.e., the one furthest away from the fabric. This lessens the reabsorption of liquid by the fabric. This is especially true if the bottom layer (layer of highest capillary pressure) is also relatively incompressible (retains a higher percentage of its void volume under pressure) compared to the top layer (layer of lower capillary pressure). In this case it may be desirable for the top layer to be resiliently compressible so as to express liquid under pressure which can be absorbed by the bottom layer.

Thus the ASRA can comprise two or more relatively distinct layers which differ in capillary pressure. As can be seen from the capillary pressure equation, a difference in capillary pressure can be achieved by varying the capillary size or the contact angle between the cleaning solution and the ASRA. Both factors can be controlled by the composition of the ASRA. The contact angle portion of the equation can also be affected by chemical treatment of the ASRA with, for example, a surfactant to lower the contact angle or a water repellent material such as silicone to increase contact angle.

The effectiveness of an ASRA comprising multiple layers of differing capillary pressure can be enhanced by locating most of the total absorbent capacity in the high capillary pressure portion. The top fabric facing layer need only be thick enough to insulate the fabric from the liquid held in the bottom layer.

The effectiveness of the layered ASRA can be further enhanced by selecting the low capillary pressure portion to have a capillary pressure higher than that of the fabric being treated.

In an ASRA comprised of two or more layers differing in capillary pressure, the pattern of capillary pressure change can be characterized as "stepped". Through the thickness of the ASRA there is a sharp change or step in capillary pressure at the layer interfaces. It will be appreciated that the ASRA herein need not comprise multiple distinct layers, but rather can comprise a single layer structure with a relatively continuous capillary size gradient through its thickness.

Fibers—The ASRA can be made from a variety of materials including fibrous absorbents and foams. Useful fibrous absorbents include nonwoven fabrics (carded, hydroentangled, thermal bonded, latex bonded, meltblown, spun, etc.), thermal bonded airlaid nonwovens ("TBAL"), latex bonded airlaid nonwovens ("LBAL"), multi-bonded airlaid nonwovens ("MBAL" combined latex and thermal bonded), wet laid paper, woven fabrics, knitted fabrics or combination of materials (i.e., top layer of a carded nonwoven, and a bottom layer of wet laid paper). These fibrous absorbents can be manufactured using a wide variety of fibers including both natural and synthetic fibers. Useful fibers include wood pulp, rayon, cotton, cotton linters, polyester, polyethylene, polypropylene, acrylic, nylon, multi-component binder fibers, etc. Multiple fiber types can be blended together to make useful materials. Useful foam materials include polyurethane foams and high internal phase emulsion foams. The critical factor is to have a difference in capillary pressure within the thickness of the ASRA. A broad range of fiber sizes can be employed. A typical, but non-limiting range of diameters is from about 0.5 micrometers to about 60 micrometers. For meltblown, the preferred fibers are less than about 10 micrometers. Typical spun-bond and synthetic staple fibers range in diameter from about 14 to about 60 micrometers. In general, one selects smaller diameter fibers for the high capillary pressure layer and higher diameters for low capillary pressure. Fiber length can depend on the forming process that is being used and the desired capillary pressure. Spun-bonds comprise a substantially continuous fiber. For air-laid fibers, 4-6 mm a is a typical fiber length. For carded fibers the fiber length range is typically 25-100 mm. In addition, enriching the upper layer in bi-component fibers may help decrease linting during use. Cleaning may also be enhanced by making the top layer rich in synthetic (e.g., bi-component) fibers due to their lipophilic nature which can aid in the removal of oily stains from the fabric being treated.

Absorbent gelling materials ("AGM") such as those sometimes referred to in the diaper art as 'supersorbers' can be added to either or both layers of the receiver or as a discrete layer between the fiber layers or on the back of the bottom layer of the ASRA. Functionally, the AGM provides additional liquid absorption capacity and serves to drain the capillaries in the ASRA structure which helps to maintain the capillary pressure gradient as liquid is absorbed.

In light of the foregoing considerations, the ASRA herein can be defined as an absorbent structure which has a capillary pressure difference through its thickness (Z-direction). In a typical, but non-limiting mode, this can be achieved by having relatively larger capillaries (for example 50-100 micrometers radius) in the upper, liquid-receiving portion of the ASRA which is placed in contact with the fabric being treated. The lower, liquid-storage portion having relatively smaller capillaries (for example 5-30 micrometers radius). Irrespective of the size employed, it is desirable that the difference in average capillary pressure between the two layers be large enough that the overlap in capillary pressure range between the two layers is minimized.

Basis Weight—The basis weight of the ASRA can vary depending on the amount of cleaning solution which must be absorbed. For example, a 127 mm×127 mm receiver absorbs about 10-50 grams of water. Since very little liquid is used in the typical stain removal process, much less capacity is actually required. A typical TBAL ASRA pad weighs about 4-6 grams. A useful range is therefore about 1 gram to about 7 grams. A variety of ASRA sizes can be used, non-limiting examples of which include 90 mm×140 mm and 127 mm×127 mm. The shape of the ASRA can also be varied.

Thickness— The overall thickness of the preferred ASRA is about 3 mm (120 mils) but can be varied widely. The low end may be limited by the desire to provide absorbency impression. A reasonable range is 25 mils to 200 mils.

Lint Control Binder Spray—The ASRA is preferably dust free. Some materials are naturally dust free (synthetic nonwoven fabrics). Some, generally cellulose containing materials, can be dusty because not all the fibers are bonded. Dust can be reduced by bonding substantially all the fibers which reside on or near the surface of the ASRA which contacts the fabric being treated. This can be accomplished by applying resins such as latex, starch, polyvinyl alcohol or the like. Cold or hot crimping, sonic bonding, heat bonding and/or stitching may also be used along all edges of the receiver to further reduce Tinting tendency.

Backing Sheet—The ASRA is generally sufficiently robust that it can be used as is. However, in order to prevent strike-through of the liquid onto the tabletop or other treatment surface selected by the user, a liquid-impermeable barrier sheet may be affixed to the bottom-most surface of the lower layer. This backing sheet also improves the integrity of the overall article. The bottom-most layer may be extrusion coated with an 0.5-2.0 mil, preferably 1.0 mil, layer of polyethylene or polypropylene film using conventional procedures. A film layer could also be adhesively or thermally laminated to the bottom layer. The film layer is designed to be a pinhole-free barrier to prevent any undesired leakage of the cleaning composition beyond the receiver. This backing sheet can be printed with usage instruction, embossed and/or decorated, according to the desires of the formulator. The ASRA is intended for use outside the dryer. However, since the receiver may inadvertently be placed in the dryer and subjected to high temperatures, it is preferred that the backing sheet be made of a heat resistant film such as polypropylene or nylon.

Colors—White is the preferred color for the ASRA as it allows the user to observe transfer of the stain from the fabric to the receiver. However, there is no functional limit to the choice of color. The backing sheet can optionally be a contrasting color.

Embossing—The ASRA can also be embossed with any desired pattern or logo.

Manufacture—A typical, but non-limiting, embodiment of the ASRA herein is a TBAL material which consists of an upper, low capillary pressure layer which is placed in liquid communication contact with the fabric being treated and a bottom high capillary pressure layer. The ASRA can be conveniently manufactured using procedures known in the art for manufacturing TBAL materials; see U.S. Pat. No. 4,640,810. TBAL manufacturing processes typically comprise laying-down a web of absorbent fibers, such as relatively short (about 2-4 mm) wood pulp fibers, in which are commingled relatively long (about 4-6 mm) bi-component fibers. The sheath of the bi-component fiber melts with the application of heat to achieve thermal bonding. The bi-component fibers intermingled throughout the wood pulp fibers thereby act to 'glue' the entire mat together. Both layers in one embodiment of the ASRA herein can be a homogeneous blend of wood pulp fibers and bi-component thermal bonding fibers. In a more preferred embodiment, the top layer is 100% concentric bi-component fiber comprising 50:50 (wt.) polyethylene (PE) and polypropylene (PP) comprising a PP core enrobed in an outer sheath of PE. The gradient is achieved by providing a higher proportion of bi-component bonding fibers in the top layer compared to the bottom layer. Using a TBAL process as described in U.S. Pat. No. 4,640,810, the top, low capillary pressure layer is formed by a first forming station from 100% bi-component fiber (AL-Thermal-C, 1.7 dtex, 6 mm long available from Danaklon a/s). Basis weight of this all-bi-component top layer is approximately 30 gsm (grams/meter$^2$). The bottom, high capillary pressure layer is formed upon the top layer by second and third forming stations from a fiber blend consisting of approximately 72% wood pulp (Flint River Fluff available from Weyerhaeuser Co.) and approximately 28% bicomponent binder fiber. Basis weight of this bottom layer is approximately 270 gsm. Each of the second and third forming station deposits approximately half of the total weight of the bottom layer. The two layers are then calendered to provide a final combined thickness of approximately 3 mm. Subsequently, a 1.0 mil coating of polypropylene is extrusion coated onto the exposed surface of the bottom layer. Individual receivers are cut to 127 mm×127 mm size. In one optional mode, since the material will be wound into a roll before applying the back sheet, a binder (e.g., latex—Airflex 124 available from Air Products) can be applied to the exposed surface of the lower layer prior to thermal bonding to prevent transfer of dust to the top all bi-component layer. Alternatively, a non-linting sheet can be placed on the ASRA during roll-up to prevent linting due to contact between the surfaces.

The composition and basis weights of the layers can be varied while still providing an ASRA with the desired capillary pressure gradient and cleaning performance.

F. Kits

In accordance with one aspect of the present invention, a kit is provided which contains the necessary materials to enable a consumer to clean an inanimate surface. In one non-limiting embodiment, the kit includes the electric stainbrush of the present invention and a cleaning solution. The kit may also include one or more absorbent stain receiver article(s). Instructions may be included with the kit that instruct the consumer how to use the kit.

The aspects and embodiments of the present invention set forth in this document have many advantages. For example, the present invention can provide improved cleaning and/or faster cleaning results on inanimate surfaces; as well as reduced fatigue on the user's fingers, hands, arms and/or shoulders.

While particular embodiments of the present invention have been illustrated and described, it would be obvious to those skilled in the art that various other changes and modifications can be made without departing from the spirit and scope of the invention. It is therefore intended to cover in the appended claims all such changes and modifications that are within the scope of this invention. All documents cited in the Detailed Description of the Invention are, in relevant part, incorporated herein by reference. The citation of any document is not to be construed as an admission that it is prior art with respect to the present invention.

What is claimed is:

1. A method of cleaning an inanimate surface comprising:
  a) having an electric stainbrush, wherein the electric stainbrush comprises
    i) a handle having a motor disposed therein;
    ii) a head having a longitudinal axis;
    iii) a neck disposed between the handle and the head;
    iv) a first bristle holder associated with the head which oscillates or rotates;
    v) a second bristle holder associated with the head which reciprocates in generally the same direction as the longitudinal axis of the head but does not rotate or oscillate and wherein the second bristle holder includes a first T-shaped block which depends from a bottom surface of the second bristle holder, wherein the T-shaded block slideably engages a first pair of projections of the head to guide the movement of the second bristle holder;
    vi) a first set of bristles associated with the first bristle holder; and
    vii) a second set of bristles associated with the second bristle holder;
    wherein the motor is operatively connected to the first and second bristle holders; and
    viii) a shaft at least partially disposed within the neck, the shaft being operatively connected to the motor and to at least to one of the first bristle holder and the second bristle holder, wherein the shaft reciprocates;
  b) putting a cleaning solution in contact with the inanimate surface; and
  c) employing the electric stainbrush to brush the cleaning solution on the inanimate surface.

2. The method of claim 1, wherein the cleaning solution is first applied to the first set of bristles, second set of bristles, or both sets of bristles; and then placed in contact with the inanimate surface.

3. The method of claim 1, wherein the second bristle holder is disposed between the first bristle holder and the handle.

4. The method of claim 1, wherein the first bristle holder only rotates or oscillates.

5. The method of claim 1, wherein the electric stainbrush further comprises a pin operatively connecting the shaft and the second bristle holder.

6. The method of claim 1, further comprising a second T-shaped block which engages a second pair of projections of the head.

7. The method of claim 1, wherein the electric stainbrush further comprises a cam associated with the shaft.

8. The method of claim 2, wherein the cleaning solution further comprises a surfactant.

9. The method of claim 5, wherein said pin engages a hole in the first T-shaped block.

10. The method of claim 7, wherein the second bristle holder includes first and second cam followers depending from a bottom surface bristle holder, the first and second cam followers being separated from one another and wherein the cam is disposed between the first and second cam followers.

11. A method of cleaning an inanimate surface comprising:
  a) having an electric stainbrush, wherein the electric stainbrush comprises
    i) a handle having a motor disposed therein;
    ii) a head having a longitudinal axis;
    iii) a neck disposed between the handle and the head;
    iv) a first bristle holder associated with the head which oscillates or rotates;
    v) a second bristle holder associated with the head which reciprocates in generally the same direction as the longitudinal axis of the head but does not rotate or oscillate wherein the second bristle holder includes a first T-shaped block which depends from a bottom surface of the second bristle holder, wherein the T-shaped block slideably engages a first pair of projections of the head to guide the movement of the second bristle holder;
    vi) a first set of bristles associated with the first bristle holder;
    vii) a second set of bristles associated with the second bristle holder, wherein the motor is operatively connected to the first and second bristle holders; and
    viii) a shaft at least partially disposed within the neck, the shaft being operatively connected to the motor and to at least to one of the first bristle holder and the second bristle holder wherein the shaft reciprocates;

b) putting a cleaning solution in contact with the inanimate surface;

c) employing the electric stainbrush to brush the solution on the inanimate surface; and d) employing an absorbent stain receiver article to remove the stain from the inanimate surface.

12. The method of claim 11, wherein the cleaning solution is an aqueous solution, a lipophilic solution, or a combination thereof.

13. A method of cleaning an inanimate surface comprising:
 a) having an electric stainbrush, wherein the electric stainbrush comprises
  i) a handle having a motor disposed therein;
  ii) a head having a longitudinal axis;
  iii) a neck disposed between the handle and the head;
  iv) a first bristle holder associated with the head which oscillates or rotates;
  v) a second bristle holder associated with the head which reciprocates in generally the same direction as the longitudinal axis of the head but does not rotate or oscillate;
  vi) a first set of bristles associated with the first bristle holder;
  vii) a second set of bristles associated with the second bristle holder, wherein the motor is operatively connected to the first and second bristle holders;
  viii) a shaft at least partially disposed within the neck, the shaft being operatively connected to the motor and to at least to one of the first bristle holder and the second bristle holder, wherein the shaft reciprocates, and wherein the shaft comprises a cam in the form of a plurality of spaced apart rings and the second bristle holder further comprises a cam follower in the form of a block having a slot disposed therein, wherein the block depends from a bottom surface of the second bristle holder and wherein the slot is shaped to receive the shaft and the block is disposed between the rings;

b) putting a cleaning solution in contact with the inanimate surface; and c) employing the electric stainbrush to brush the cleaning solution on the inanimate surface.

14. A method of cleaning an inanimate surface comprising:
 a) having an electric stainbrush, wherein the electric stainbrush comprises
  i) a handle having a motor disposed therein;
  ii) a head having a longitudinal axis;
  iii) a neck disposed between the handle and the head;
  iv) a first bristle holder associated with the head which oscillates or rotates;
  v) a second bristle holder associated with the head which reciprocates in generally the same direction as the longitudinal axis of the head but does not rotate or oscillate;
  vi) a first set of bristles associated with the first bristle holder;
  vii) a second set of bristles associated with the second bristle holder, wherein the motor is operatively connected to the first and second bristle holders;
  viii) a shaft at least partially disposed within the neck, the shaft being operatively connected to the motor and to at least to one of the first bristle holder and the second bristle holder, wherein the shaft reciprocates, and wherein the shaft comprises a pair of projections which extend in a direction transverse from the shaft and wherein the second bristle holder further comprises a block depending from a bottom surface of the second bristle holder having a pair of slots which are shaped to slideably receive the projections;

b) putting a cleaning solution in contact with the inanimate surface; and c) employing the electric stainbrush to brush the cleaning solution on the inanimate surface.

\* \* \* \* \*